(12) United States Patent
Halliday et al.

(10) Patent No.: US 12,156,595 B1
(45) Date of Patent: Dec. 3, 2024

(54) MATTRESS AND ASSOCIATED METHODS FOR PROVIDING CUSTOMIZED SPINE AND BODY SUPPORT

(71) Applicants: Steven R. Halliday, Salem, UT (US); Michael V. Halliday, Salem, UT (US)

(72) Inventors: Steven R. Halliday, Salem, UT (US); Michael V. Halliday, Salem, UT (US)

(*) Notice: Subject to any disclaimer, the term of this patent is extended or adjusted under 35 U.S.C. 154(b) by 389 days.

(21) Appl. No.: 17/496,634

(22) Filed: Oct. 7, 2021

Related U.S. Application Data

(63) Continuation-in-part of application No. 16/274,794, filed on Feb. 13, 2019, now abandoned.

(60) Provisional application No. 63/253,334, filed on Oct. 7, 2021, provisional application No. 62/631,026, filed on Feb. 15, 2018, provisional application No. 62/631,002, filed on Feb. 15, 2018.

(51) Int. Cl.
| | |
|---|---|
| *A47C 27/05* | (2006.01) |
| *A47C 27/00* | (2006.01) |
| *A47C 27/14* | (2006.01) |
| *A61B 5/00* | (2006.01) |

(52) U.S. Cl.
CPC .......... *A47C 27/146* (2013.01); *A47C 27/002* (2013.01); *A47C 27/05* (2013.01); *A61B 5/4561* (2013.01)

(58) Field of Classification Search
CPC ..... A47C 27/146; A47C 27/002; A47C 27/05; A61B 5/4561
See application file for complete search history.

(56) References Cited

U.S. PATENT DOCUMENTS

| | | | |
|---|---|---|---|
| 5,513,402 A | * | 5/1996 | Schwartz ............. A47C 27/001 5/691 |
| 7,120,956 B1 | | 10/2006 | Liao |
| 7,321,811 B1 | | 1/2008 | Rawls-Meehan |
| 7,465,280 B2 | | 12/2008 | Rawls-Meehan |
| 7,841,031 B2 | | 11/2010 | Rawls-Meehan |
| 7,854,031 B2 | | 12/2010 | Rawls-Meehan |
| 7,860,723 B2 | | 12/2010 | Rawls-Meehan |
| 7,861,342 B1 | | 1/2011 | Huang |
| 7,930,783 B2 | | 4/2011 | Rawls-Meehan |
| 7,979,169 B2 | | 7/2011 | Rawls-Meehan |
| 8,020,230 B2 | | 9/2011 | Rawls-Meehan |
| 8,028,363 B2 | | 10/2011 | Rawls-Meehan |
| 8,046,116 B2 | | 10/2011 | Rawls-Meehan |
| 8,078,337 B2 | | 12/2011 | Rawls-Meehan |

(Continued)

*Primary Examiner* — Myles A Throop
(74) *Attorney, Agent, or Firm* — Workman Nydegger

(57) ABSTRACT

A mattress and method custom fitted to a user. The mattress includes a top cover zippered over a top of the mattress, and an encasement extending beneath the top cover, having a sidewall extending up and around an outer perimeter of the encasement. The mattress includes a plurality of support layer foam pads or strips positionable in the encasement, on a sub-layer thereof so that the sidewall of the encasement extends around an outer perimeter of the pads/strips. At least one of the pads/strips provides a different level of firmness relative to a level of firmness provided by another of the pads/strips, and the pads/strips are removable from the encasement. The pads/strips allow customization of the sleep surface, so that customized firmness (i.e., support) is provided, particularly in the lumbar region of the spine, to ensure no more than ¾ inch of compression in the lumbar support layer strip occurs.

20 Claims, 10 Drawing Sheets

(56) References Cited

U.S. PATENT DOCUMENTS

| | | |
|---|---|---|
| 8,181,296 B2 | 5/2012 | Rawls-Meehan |
| 8,375,488 B2 | 2/2013 | Rawls-Meehan |
| 8,565,934 B2 | 10/2013 | Rawls-Meehan |
| 8,682,457 B2 | 3/2014 | Rawls-Meehan |
| 8,869,328 B2 | 10/2014 | Rawls-Meehan |
| 8,909,357 B2 | 12/2014 | Rawls-Meehan |
| 8,909,378 B2 | 12/2014 | Rawls-Meehan |
| D720,553 S | 1/2015 | Rawls-Meehan |
| 8,926,535 B2 | 1/2015 | Rawls-Meehan |
| 9,003,584 B2 | 4/2015 | Rawls-Meehan et al. |
| 9,031,673 B2 | 5/2015 | Rawls-Meehan |
| 9,044,365 B2 | 6/2015 | Rawls-Meehan |
| 9,044,366 B2 | 6/2015 | Rawls-Meehan |
| 9,066,497 B2 | 6/2015 | Rawls-Meehan |
| 9,131,782 B1 * | 9/2015 | Baker ................ A47C 27/001 |
| 9,144,320 B1 * | 9/2015 | Baker ................ A47C 27/064 |
| 9,289,074 B1 * | 3/2016 | Corbin ................ A47C 27/15 |
| 9,504,336 B2 * | 11/2016 | Dodd ................ A47C 19/025 |
| 10,039,388 B2 | 8/2018 | Murphy et al. |
| 2007/0022540 A1 * | 2/2007 | Hochschild .......... A47C 27/001 |
| | | 5/738 |
| 2007/0283501 A1 * | 12/2007 | Mossbeck ............. A47C 27/00 |
| | | 5/690 |
| 2008/0201856 A1 * | 8/2008 | Howard .............. A47C 31/123 |
| | | 5/690 |
| 2015/0089747 A1 | 4/2015 | Ni et al. |
| 2016/0270548 A1 * | 9/2016 | Corbin ................ A47C 27/15 |
| 2017/0325596 A1 * | 11/2017 | Torbet ................ A47C 27/14 |

* cited by examiner

MATTRESS AND ASSOCIATED METHODS FOR PROVIDING CUSTOMIZED SPINE AND BODY SUPPORT

CROSS-REFERENCE TO RELATED APPLICATIONS

The present application claims priority to and the benefit of U.S. Patent Application No. 63/253,334, filed Oct. 7, 2021, which is herein incorporated by reference in its entirety. The present application is also a continuation-in-part of U.S. patent application Ser. No. 16/274,794 filed Feb. 13, 2019, which claims priority to and the benefit of U.S. Patent Application Ser. Nos. 62/631,002 and 62/631,026 both filed Feb. 15, 2018, each of which is herein incorporated by reference in its entirety.

BACKGROUND OF THE INVENTION

1. The Field of the Invention

The present invention relates generally to mattresses and associated methods for providing customized spine and body support to a sleeper.

2. Background and Relevant Art

The mattress and bed industry provides numerous options for sleep to users, and individual manufacturers promote various options provided by their particular mattress system. For example, various bed and mattress options are provided using differing materials for support of the sleeper, and various mechanisms for sometimes altering the firmness or softness characteristics of a given mattress. Still, even with the numerous options available, many individuals find it difficult to find a mattress that will consistently provide them with a good night's sleep, and a desired level of support for their body, particularly at a moderate price. As such, there is a continuing need in the field for improved mattresses and methods that would address such problems.

BRIEF SUMMARY

While there are numerous materials available for mattress construction, particularly those materials that are used to support the weight and pressure exerted by a user sleeping on a mattress, e.g., a foam layer over coils, memory foam, inflatable air chamber mattresses, water beds, and the like, many consumers find that even if they replace their bed, and are happy with whatever new mattress they purchase, that that satisfaction is short-lived, and within a short number of weeks, months, or perhaps years (e.g., 2-5 years) in the best cases, they have the same issues they may have complained of previously, or new issues. Back pain upon waking is a very common complaint, and is indicative of improper support being provided by the mattress to the sleeper.

Furthermore, while various mattress options are sometimes available that may allow a user to adjust the overall firmness or softness provided in their mattress (or on a single side of a queen or king size mattress), there are very few, if any options that are commercially available that provide differing levels of firmness within a single sleep surface designated for a given user. For example, while some systems (e.g., such as a SLEEP NUMBER mattress) may allow a user to make one side or the other of their queen or king size mattress harder or softer, there are no existing commercially available systems that would provide greater firmness to specific, targeted areas to a user sleeping on the mattress, while at the same time providing relatively softer support to other targeted areas for that same user. For example, such a system may provide a user with relatively firm support in the lumbar curve region of the lower back and spine, and softer, less firm support in the region of the shoulders and calves.

Furthermore, even though in theory, systems may have been proposed (e.g., such as in US2008/0201856 to Howard) that may superficially appear to provide some degree of customizability and adjustability in the firmness provided to specific areas of a given sleep surface on a mattress, the proposed implementations of the system in Howard and other similar art is insufficient to address the problems noted above.

For example, in Howard, the firmness of the coil spring core cartridges 26 is based on "zonal weight", "sleep habits", and "body measurements" (particularly width measurements of the "wrist", "shoulder", user "height", "hips" and "waist"). There is no suggestion in Howard or elsewhere for a more rigorous scientific approach, where the selection of firmness and positioning is based on spinal curvature measurements taken from the patient. While Howard may mention in paragraph 72-73 that a spine neutral fit is desired, the configuration provided in Howard is incapable of ensuring that any such fit is consistently provided, particularly in a manner that will last. In the present configurations, the selection of the firmness of a support layer strip placed under the lumbar region of the user's spine is based on an actual spinal curvature measurement (not zonal weights, or the other parameters relied on in Howard), and the selection of such support layer strip is selected to ensure that no more than ¾ inch (more particularly no more than ⅝ inch) of compression or "sag" occurs during use by the user.

Furthermore, the support layer strips and pads that provide the variable firmness on the sleep surface of the mattress are regularly monitored, as due to normal wear, the support layer pads and strips will eventually need replacement, even with regular rotation of such pads and strips. Once such regularly monitored measurements show that more than ¾ inch (or ⅝ inch) compression or "sag" has occurred, the worn out pads and/or strips are replaced.

It is critical to the invention that the support layer pads, and particularly the support layer strip which is positioned under the lumbar region of the user's spine during use of the bed, be configured to ensure that no more than ¾ inch, ideally no more than ⅝ inch of compression or sag occurs. Such feature is critical as Applicant has found that when more compression than this occurs, then a host of problems associated with back pain and the like tend to occur.

Another important feature of the present invention is that the foundation layer that supports the support layer be provided by pocketed coil springs, e.g., where the pocketed coil springs provide uniform firmness across the sleep surface (typically across the entire mattress in a queen or king size mattress), and that the variable firmness layer be in the top portion of the mattress, rather than in the bottom portion of the mattress, as in Howard. For example, in Howard, the difference in firmness values is provided within the layer of pocketed coil springs (by pocketed coil spring cartridges 26), which cartridges providing the variable firmness layer are covered over by foam layer 24b and also topper foam cartridges 38 and 40. Such foam layers over the variable firmness support layer is counterproductive to a goal of providing differences in firmness along the sleep surface, as any customized or varying firmness provided along the sleep surface by differences in firmness of cartridges 26 is lost by providing significant thickness of foam layers thereover. This results in the inability to deliver the required firmness where needed, particularly under the lumbar region of the spine.

The present configuration differs in that it provides a top cover removably attached to a remainder of the mattress by a zipper, an encasement extending beneath the top cover and having a sidewall extending up and around an outer perimeter of the encasement, and a customizable support layer comprising a plurality of support layer foam pads and/or strips disposed in the encasement, on a sub-layer of the encasement so that the sidewall of the encasement extends around an outer perimeter of the plurality of support layer foam pads or strips, wherein at least one of the support layer foam pad strips provides a different level of firmness relative to a level of firmness provided by another of the support layer foam pad strips. Each of the support layer foam pad strips are individually removable from the encasement. A plurality of pocketed coil springs are provided below the sub-layer of the encasement, where the pocketed coil springs do not provide any variable firmness across the sleep surface of the mattress, but are uniformly configured to provide a uniform level of firmness across the sub-layer of the encasement. Particular support layer foam pads are selected and positioned in the encasement on the sublayer, in a customized arrangement customized to the individual user, to provide a different level of firmness for the user from head to foot along the sleep surface. Importantly, selection and positioning of the support layer foam pads or strips are not determined based on user preference, or on zonal weights, or other criteria mentioned in Howard and similar art. Rather, selection and positioning is based on the measurement of the curvature of the spinal region of the user's back, such that a sleep surface is custom created in which the support layer foam pad strips provide different levels of firmness to different regions of the user's body from head to foot when laying on the sleep surface of the mattress, based on the measurement of the curvature of the spinal region of the person's back. Critically, as described above, the support layer pads or strips as a whole, and particularly the support layer strip positioned under the lumbar region of the user's spine are configured to ensure that no more than ¾ inch of compression or "sag" occurs.

As noted, the method can further include regular maintenance by which the pads or strips are flipped over and/or rotated (where each side of a given strip or pad provides the same firmness, rather than providing different firmness values associated with a given face of the pad or strip). In addition, measurements can be taken on the mattress as a whole, or the support pads, to determine how much compression or "sag" has occurred or is occurring. Once the degree of compression or sag equals ¾ inch, or ⅝ inch, the support layer pad or strip exhibiting too much compression or sag is replaced.

These and other advantages and features of the present invention will become more fully apparent from the following description and appended claims, or may be learned by the practice of the invention as set forth hereinafter.

BRIEF DESCRIPTION OF THE DRAWINGS

While the specification concludes with claims particularly pointing out and distinctly claiming that which is regarded as the present invention, the advantages of embodiments of the disclosure may be more readily ascertained from the following description when read in conjunction with the accompanying drawings.

DETAILED DESCRIPTION OF THE PREFERRED EMBODIMENTS

I. Definitions

Figure 1:
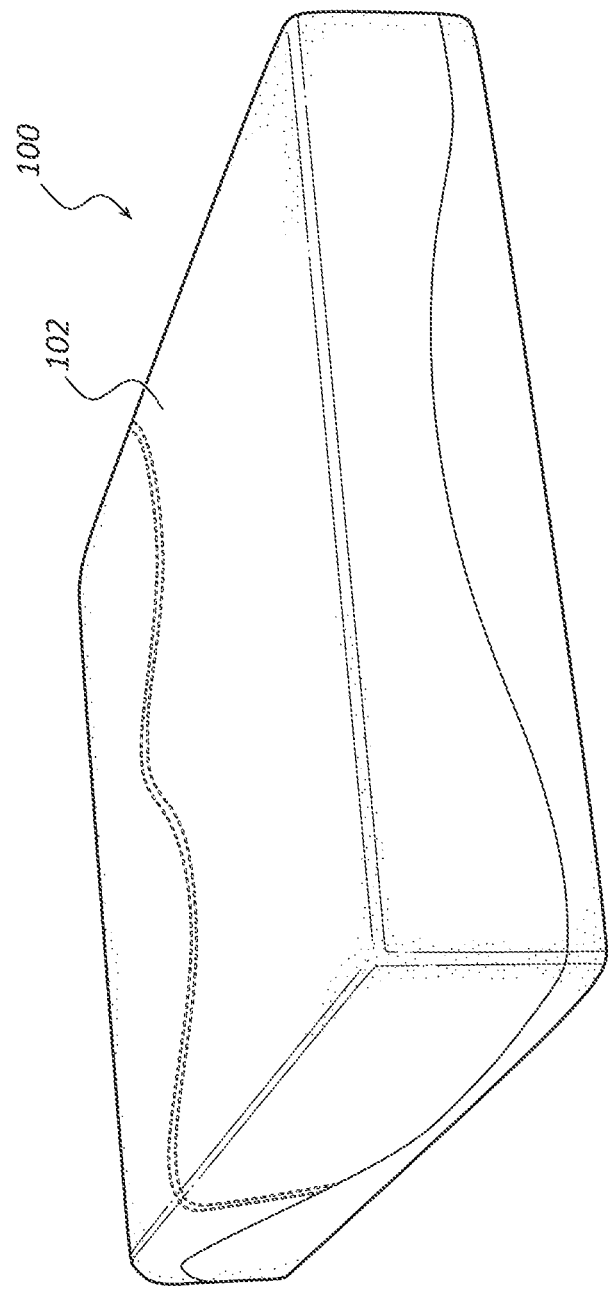
FIG. 1 is perspective exterior view of an exemplary mattress.

All publications, patents and patent applications cited herein are hereby incorporated by reference in their entirety to the same extent as if each individual publication, patent or patent application was specifically and individually indicated to be incorporated by reference. For example, any of the conditions or starting materials described in the inventor's earlier applications, already referenced, may be adapted for use according to the methods, metal carbide fibers, or articles disclosed herein.

Numbers, percentages, or other values stated herein are intended to include that value, and also other values that are about or approximately the stated value, as would be appreciated by one of ordinary skill in the art encompassed by embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 10%, within 5%, within 1%, within 0.1%, or within 0.01% of a stated value. As such, all values are understood to be modified by the term "about".

Ranges between any values disclosed herein are contemplated and within the scope of the present disclosure (e.g., a range defined between any two values (including end points of a disclosed range) given as exemplary for any given parameter).

As used in this specification and the appended claims, the singular forms "a," "an" and "the" include plural referents unless the context clearly dictates otherwise.

As used herein, the terms "comprising," "including," "containing," "characterized by," and grammatical equivalents thereof are inclusive or open-ended terms that do not exclude additional, unrecited elements or method steps, but also include the more restrictive terms "consisting of" and "consisting essentially of" and grammatical equivalents thereof.

II. Exemplary Systems and Methods

While there are numerous materials available for mattress construction, particularly those materials that are used to support the weight and pressure exerted by a user sleeping on a mattress, e.g., a foam layer over coils, memory foam, inflatable air chamber mattresses, water beds, and the like, many consumers find that even if they replace their bed, and are happy with whatever new mattress they purchase, that that satisfaction is short-lived, and within a short number of weeks, months, or perhaps years (e.g., 2-5 years) in the best cases, they have the same issues they may have complained of previously, or new issues. Back pain upon waking is a very common complaint, and is indicative of improper support being provided by the mattress to the sleeper.

Furthermore, while various mattress options are sometimes available that may allow a user to adjust the overall firmness or softness provided in their mattress (or on a single side of a queen or king size mattress), there are very few, if any options available that provide differing levels of firmness within a single sleep surface designated for a given user. For example, while some systems (e.g., such as a SLEEP NUMBER mattress) may allow a user to make one side or the other of their queen or king size mattress harder or softer, there are no existing systems that would provide greater firmness to specific, targeted areas to a user sleeping on the mattress, while at the same time providing relatively softer support to other targeted areas for that same user. For example, such a system may provide a user with relatively firm support in the lumbar curve region of the lower back and spine, and softer, less firm support in the region of the shoulders and calves. While some general concepts relative to providing different levels of firmness within a given sleep surface of a mattress may be suggested in Howard or similar art, the implementation of the system in Howard and others is problematic, in that they do not actually address the key problems addressed by the mattress systems and methods described herein.

Because every individual has a uniquely shaped spine, as well as where they habitually rest themselves on their mattress (e.g., closer to the top of the mattress, or if they tend to slide downward, more towards the bottom of the mattress), it is impossible to provide a mass-manufactured mattress that would work for every individual, as some customization would be needed to ensure that the increased firmness is provided where needed, and relatively softer support is also provided where needed. The placement of such regions of different firmness cannot simply be based on user preference, or on measurement of zonal weights, height, waist, hip measurements, and the like, as suggested in Howard and similar art, if the mattress is going to address the problems in the art.

Furthermore, existing mattress systems are not well suited to allowing refurbishment of components of the mattress that may wear out fastest, particularly where other components of the mattress may last far longer, even decades. As such, typical mattresses, particularly those based on providing support through foam padding, are not adapted for such refurbishing, but are instead simply thrown out in their entirety after typically 5 to 10 years, when the user becomes so frustrated with their sleep experience that they replace the mattress. Evidence of such degradation of the mattress is found in the fact that many hotel chains mandate mattress replacement every 5 years in an effort to ensure a high level of customer satisfaction.

The present mattresses are specifically configured to provide customized support to a user, with differing levels of firmness along the length of the sleep surface of the bed, and where a support layer strip of a needed firmness is positioned under the lumbar region of the user's spine, where selection and positioning of the lumbar support layer strip is determined based on measurements of the user's spinal curvature, rather than other parameters (e.g., zonal weights and customer preference, which are the principal criteria in Howard). In a queen or king mattress intended to accommodate two sleepers, one on each side, the mattress may provide two sleep surfaces, with each one independently customized or customizable to the particular individual who will be sleeping thereon. In particular, the support layer strip positioned under the lumbar region of the user's spin ensures that no more than ¾ inch, or no more than ⅝ inch of compression or "sag" occurs during use by the user. The support layer may be regularly monitored, so that when the support layer pads and/or strips (particularly the all-important lumbar strip) begin to exhibit too much compression or sag due to wear, they are replaced.

It is also important that the support layer pads and strips providing customizable firmness characteristics to different regions of the sleep surface be provided in the top portion of the mattress, above the pocketed coil springs, which provide a firm foundation for the support layer pads and strips, and the underlying sublayer of the encasement separating the pocketed coil springs from the support layer pads and strips. It is important that the support layer pads and strips be essentially the top foam padding layer of the mattress, to ensure that the customized firmness provided by such support layer is not "watered down" by significant additional padding, above such support layer. As such, while there may be a simple zippered quilted topper over the support layer pads and strips, such layer is thin by comparison to the other padding layers in the mattress, e.g., including no more than 1 inch, or no more than ½ inch of padded thickness. In contrast, Howard includes multiple layers 24b and 38/40 over their layer providing customized firmness, which defeats the purpose of such customization, severely dampening and over cushioning any customization of the firmness, due to the several inches of foam padding provided over such layer. Such a configuration makes it impossible to provide precision tailored firmness characteristics where significantly greater firmness is provided directly under the lumbar region of the spine, as compared to the firmness provided on either side. It also interferes with the ability to ensure that no more than ¾ inch, or no more than ⅝ inch of compression or sag occurs during use.

An embodiment of the mattress may include a top cover that may be removably attached over a top of the mattress (e.g., by a zipper, or otherwise). As noted above, the support layer providing varying firmness from head to foot along the sleep surface of the mattress may be positioned directly beneath the top cover, without any other structures interposed therebetween. This allows easy adjustment of the support layer by simply unzipping the top cover. It also ensures that the prescribed firmness values are delivered from the support layer to the user, with only the thin top cover interposed therebetween, minimizing "watering down" of delivery of the prescribed firmness to the user's back.

The mattress may include an internal encasement that extends beneath the top cover, and includes a sidewall extending up and around an outer perimeter of the encasement. The mattress may further include a customizable support layer made up of a plurality of support layer foam pads or strips that are positioned or positionable in the encasement, on a sub-layer thereof. Placement of the foam pad strips on the sub-layer positions the strips in the encasement, with the sidewall of the encasement extending around an outer perimeter of the foam pad strips (the perimeter being provided by the collective pads, all together). At least one of the pad strips provides a different level of firmness relative to a level of firmness provided by another of the pad strips, and each pad strip is configured to be removed from the encasement (e.g., they are placed loose in the encasement, not glued, or otherwise anchored in place, to the sub-layer or side walls). In an embodiment, the support layer strip positioned under the lumbar region of the user's spine is firmer than the support layer pads or strips on the top and bottom thereof. The pads and strips may simply be held in place as a result of a friction fit provided by all of the pads and strips being aligned, in the space on the sublayer, between the sidewalls of the encasement as shown in the Figures.

Another embodiment is directed to methods for customizing support provided by such a mattress to an individual user. Such a method may begin by measuring a curvature of a spinal region of a person's back. Such measurement may also be a critical feature of the method, as the selections and positioning made thereafter are based on such a definitive measurement, not on user preference, zonal weights, or other parameters which are not sufficient to address problems of lower back pain that are addressed by the present invention. A customizable mattress including a customizable support layer as described herein is also provided according to such a method. Such a mattress may include a top cover removably attached over a remainder of the mattress by, e.g., a zipper, and an encasement beneath the top cover, having a sidewall and a sub-layer. The sidewall may extend up and around a perimeter of the encasement, defining a cavity therein, into which the support layer foam pads or strips of the customizable support layer may be placed in a custom arrangement, based on the spinal curvature measurement. The plurality of support layer foam pads and strips are positionable on the sub-layer, in the encasement, so as to be surrounded along the perimeter of the mattress by the sidewalls of the encasement. The foam pads or strips are advantageously provided in varying levels of firmness. For example, one of the pads or strips provides a level of firmness that is different from that provided by another of the pads or strips. For example, the pads or strips may be numbered or otherwise coded to indicate their level of firmness (e.g., 1-5, where 1 is very soft, and 5 is very firm). Pocketed coil springs may be positioned below the sub-layer of the encasement, providing a uniform level of firmness across the sub-layer of the encasement. Importantly, the variable customized firmness levels are provided in the support layer pads at the top of the mattress, not in the pocketed coil springs.

Based on the measurements taken of the user's spinal region, the pads and strips may be placed in the encasement, creating a specific arrangement of relatively softer and relatively harder pads or strips down the sleep surface, based on the measurements taken. For example, the lumbar region of the spine may be positioned over a relatively firmer strip (e.g., a "3" or "4" or "5"), while other areas of the spine and other body portions may be supported with softer pads or strips. For example, "1" or "2" firmness pads or strips may be placed under the user's shoulders, head, and/or calves. The neck may for example be supported with a strip having a relative firmness value of "2" or "3". In an embodiment, a strip of relatively narrow width is placed under the lumbar region of the spine, while wider pads are positioned above and/or below such narrow lumber strip. This allows for placement of a narrow strip of significantly greater firmness under the lumbar region of the spine (e.g., no more than 12 inches, no more than 10 inches, no more than 8 inches, or no more than 6 inches, such as 2-6 inches), while providing a wider pad (more than 12 inches, more than 14 inches, such as 20-30, or about 24 inches wide) of uniform firmness above (towards the head) or below (towards the feet) the lumbar strip. Such narrow support layer members may be termed strips, while the wider support layer members may be termed pads, for instance. The particular arrangement may also account for where on the sleep surface the user typically lays (e.g., more up, or more down), whether the user sleeps on their back, on either side, or on their stomach, or the like. Such variables can be accounted for in the particular arrangement of pads and strips that is installed in the interior of the mattress, directly under the cover. As noted herein, it is important that the support layer strip and any pads in the central portion of the support layer (i.e., the "crush zone") ensure that no more than ¾ inch, or no more than ⅝ inch of compression or sag occurs during use by the user. The support layer, particularly the crush zone region thereof, can be regularly evaluated, to ensure that as the pads and strips wear, even with regular rotation and flipping, that once the pads to begin to approach or show ¾ inch, or ⅝ inch of compression or sag, that they are replaced. By way of example, the timeline for when this may occur may depend on the weight of the user, and other factors, but generally speaking, even where regular rotation and flipping of pads and strips occurs, such replacement may be needed within 4 years, or even within 2 years of initial use. The system advantageously allows replacement of these minor and relatively inexpensive components, rather than the typical solution of throwing out the entire mattress and purchasing a new one.

The system thus provides customized firmness along the sleep surface associated with the mattress. While a twin-size mattress may only include a single sleep surface, larger mattresses, such as queen or king-size mattresses, will include two sleep surfaces. Each sleep surface defined by the mattress includes its own set of support layer foam pads and strips, forming a customized arrangement of varying firmness and softness from the head location of the sleep surface, through the neck location, the shoulders location, the torso location, the lumbar region of the spine location, the hip location, the thigh location, the knee location, the calves location, and the feet location of the sleep surface. Each such location may potentially include its own customized firmness value, as set by the firmness value of the particular strip used to fill that portion of the encasement, in which the strips are housed.

For example, each sleep surface may typically include 3-20 such pads and/or strips, each potentially of a differing firmness (or at least differing from that of adjacent pads or strip(s)). By way of further example, a particularly useful embodiment may include 3 wider pads and 2 narrower strips for each sleep surface (10 total per mattress). One strip may be positioned at the top position in the support layer, with the other positioned under the lumbar region of the user's spine. The pads may be positioned with one between the two strips, and the other two below (towards the feet) the lumbar strip.

The top position strip may serve as a spare lumbar strip, allowing the user to swap that strip for the lumbar strip at regular intervals (e.g., once or twice a month). Other configurations of pads and/or strips are of course also possible. Each strip may be about 5 inches wide, and the full width of the recess defined in the encasement for a twin mattress, or half the width of the same recess for a queen or king size mattress. The pads and strips may be about 2 inches thick, although it will be appreciated that dimensions may of course be varied (e.g., width of from 2-24 inches wide, or 2 to 10 inches wide, and thicknesses may be from 1 inch to 4 inches, or 2 to 3 inches thick). The mattress may include numbers, colors, letters, or other indicia on the foam pad strips identifying the firmness of the particular pad or strip. Such pads and strips may be formed of conventional high resiliency (HR) latex foam such as that typically used in a mattress support layer. A key difference is that the support layer here is provided by individual pads and strips providing different firmness characteristics, so that the firmness of the support layer actually changes as one moves from the head location of the sleep surface to the foot location of the sleep surface, with that change being provided as a result of actual measurements taken on the user's spinal region, and where it is critical that the selections are made to ensure no more than ¾ inch, or no more than ⅝ inch of compression or sag in the support layer foam during us by the user.

As noted, it is important that no significant padding layer be provided above the support layer provided by the pads and strips, other than the relatively thin batting pillow layer (e.g., fiber batting) included in the top cover that zips over the support layer. In other words, in an embodiment, there is no or only a minimal layer of foam padding positioned over the support layer, to minimize "watering down" of the prescriptive firmness values provided in the support layer, to the user's back. The top cover is easily washable upon removal of the top cover from the remainder of the mattress. The bottom portion of the cover may similarly be washable, without any significant foam layers if desired. By not including any additional padding or other layers (other than the zippered cover) over the support layer provided by the numbered foam pads or strips, the strips are also more easily accessible for replacement, adjustment, etc. by simply unzipping the top cover, without having to dig deeper to make any adjustments (as would be the case in Howard, where the customization is in the pocketed coil spring layer).

The figures further illustrate how a king or queen size mattress includes two sleep surfaces, with two sets of customizable support surfaces provided by a plurality of the strips. The particular arrangement of numbers (and thus firmness associated with a given strip, and corresponding location of the support layer) is customizable, as shown. Each sleep surface can independently include a different arrangement of numbered pads and strips, so as to be customized to the particular needs of the person sleeping on that particular side of the mattress. The particular measurements taken of the spinal region are identical or similar to those described in Applicant's issued U.S. Pat. Nos. 8,740, 303 and 9,254,042, each of which is herein incorporated by reference in its entirety. In the before mentioned patents, the measurements of the spinal region were used to customize a chair or backrest member for use with a chair, to the particular person being measured. In the present context, the measurements are used to customize firmness and placement of the pads and strips in the encasement of the mattress, e.g., to ensure placement of proper support under the neck, at the shoulders, for the hips, and particularly for the lumbar region of the spine.

Figure 2:
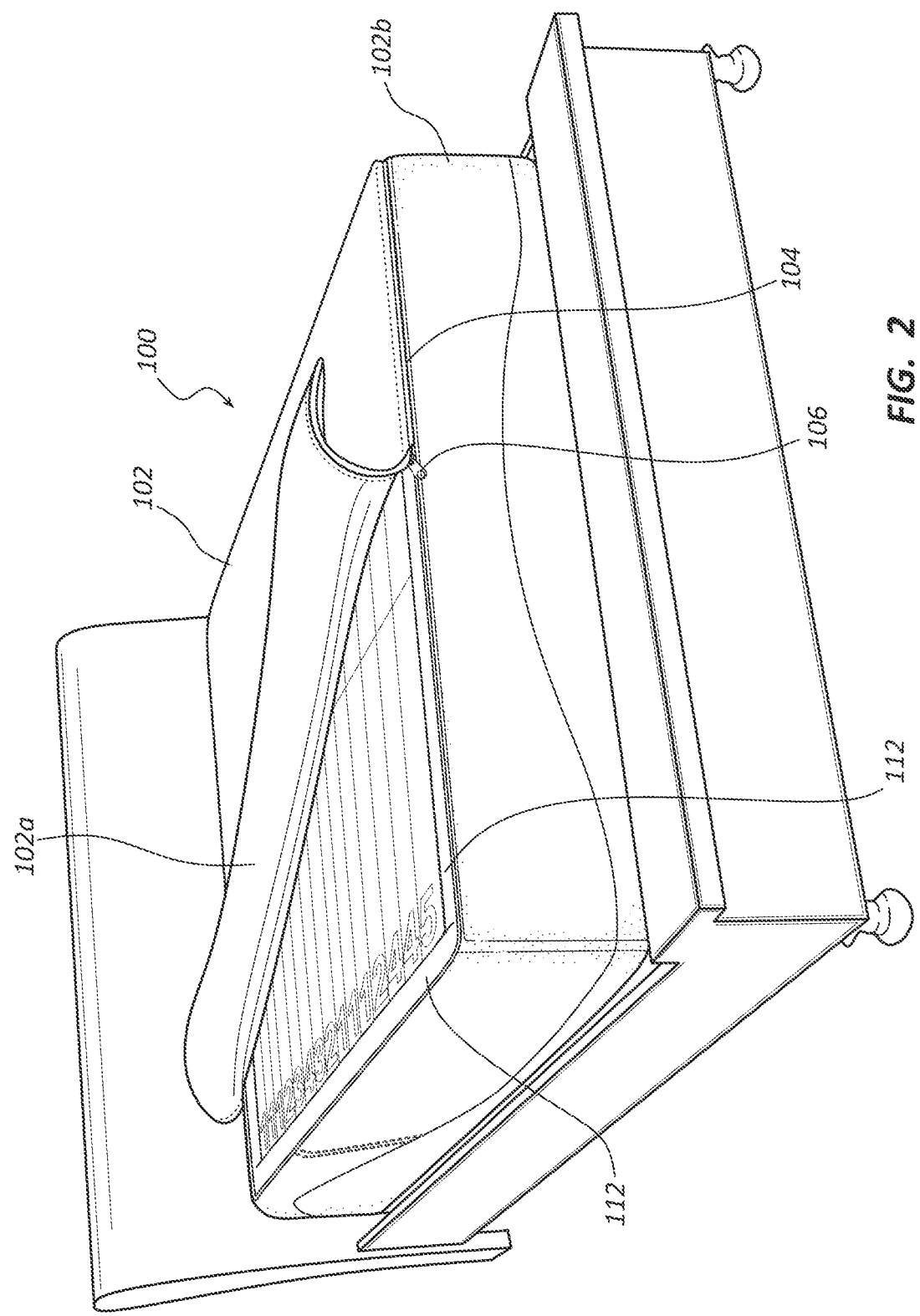
FIG. 2 shows the mattress of FIG. 1, in which the top has been zipped open, showing the plurality of support pads disposed thereunder.

For example, FIG. 2 on the left side sleep surface, shows placement of very firm support (the strip labeled "4") corresponding to the positioning of the lumbar region of the spine (6th strip down from the top), with "3" strips on either side thereof. The "2" strip seen above the higher "3" strip already corresponds to the position of the shoulders. Below the lumbar "4" strip, there is a "3", followed by a "2" and then a series of "1" strips, which may correspond to the hips (where softer support would be desired, as with the shoulders). Further down the sleep surface, there are additional values of strips at the very foot of the mattress. The arrangement seen in FIG. 2 (as well as that seen in the other Figures) is entirely customizable. While the opposite sleep surface of the bed is now fully uncovered, it is apparent that the strips (or pads) on that side can be fully customized, to meet the needs of the sleep partner on that side.

Figure 3:
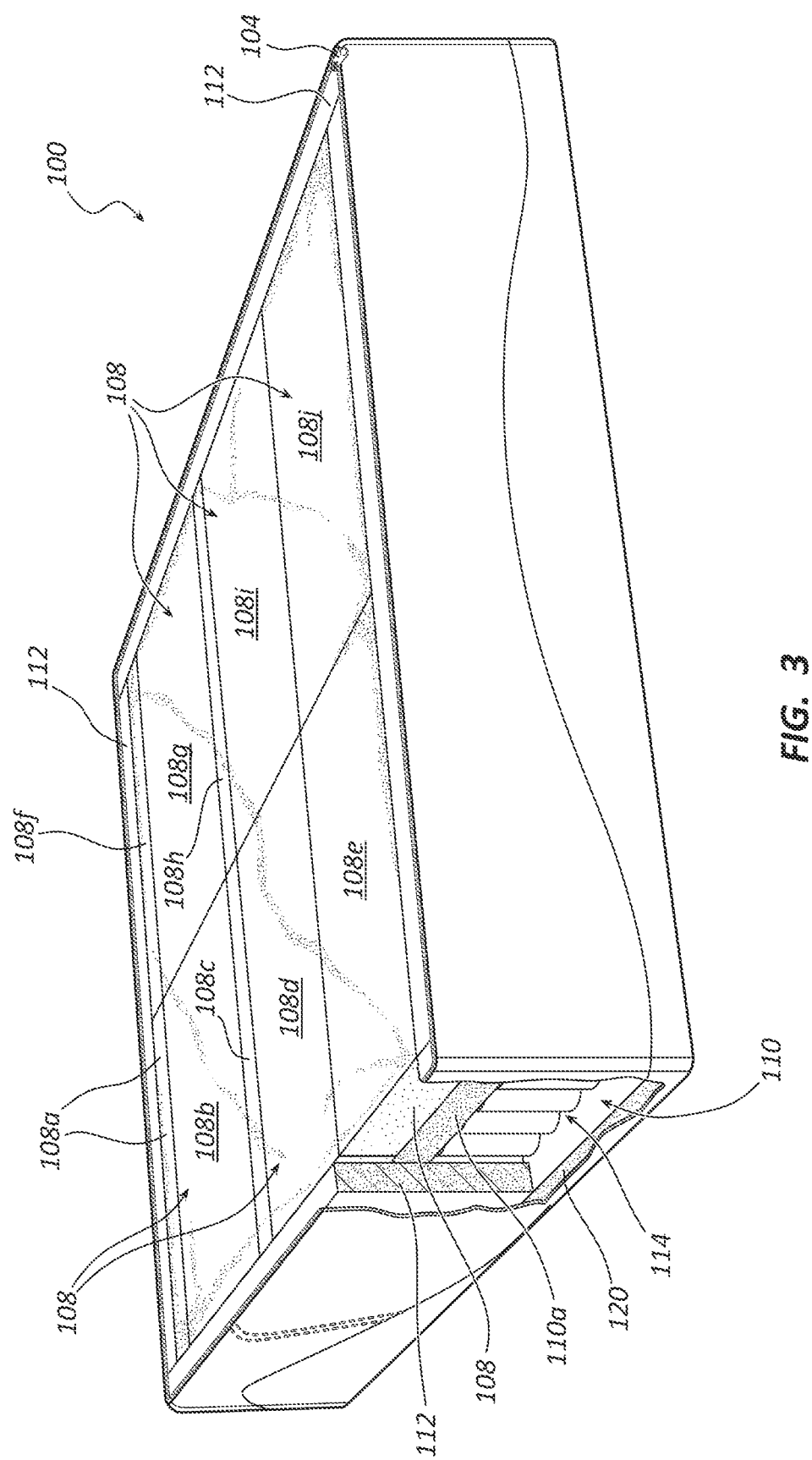
FIG. 3 shows a schematic cut-away window on the side of the mattress to illustrate the inner layers of the mattress, including the plurality of pads disposed under the top cover.
Figure 9:
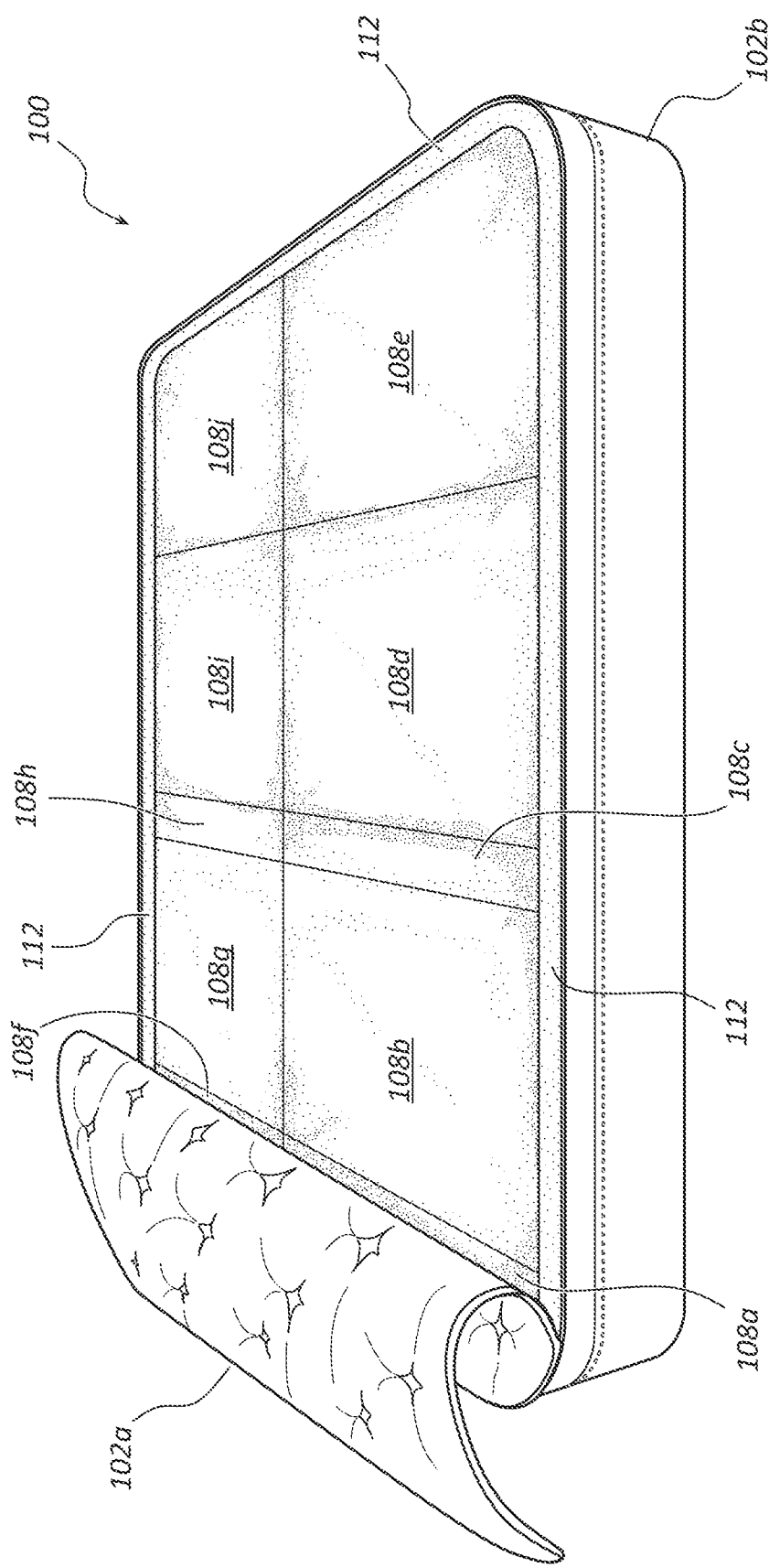
FIG. 9 illustrates a mattress that includes a top cover that has been at least partially removed to expose a plurality of support layer pads.
Figure 10:
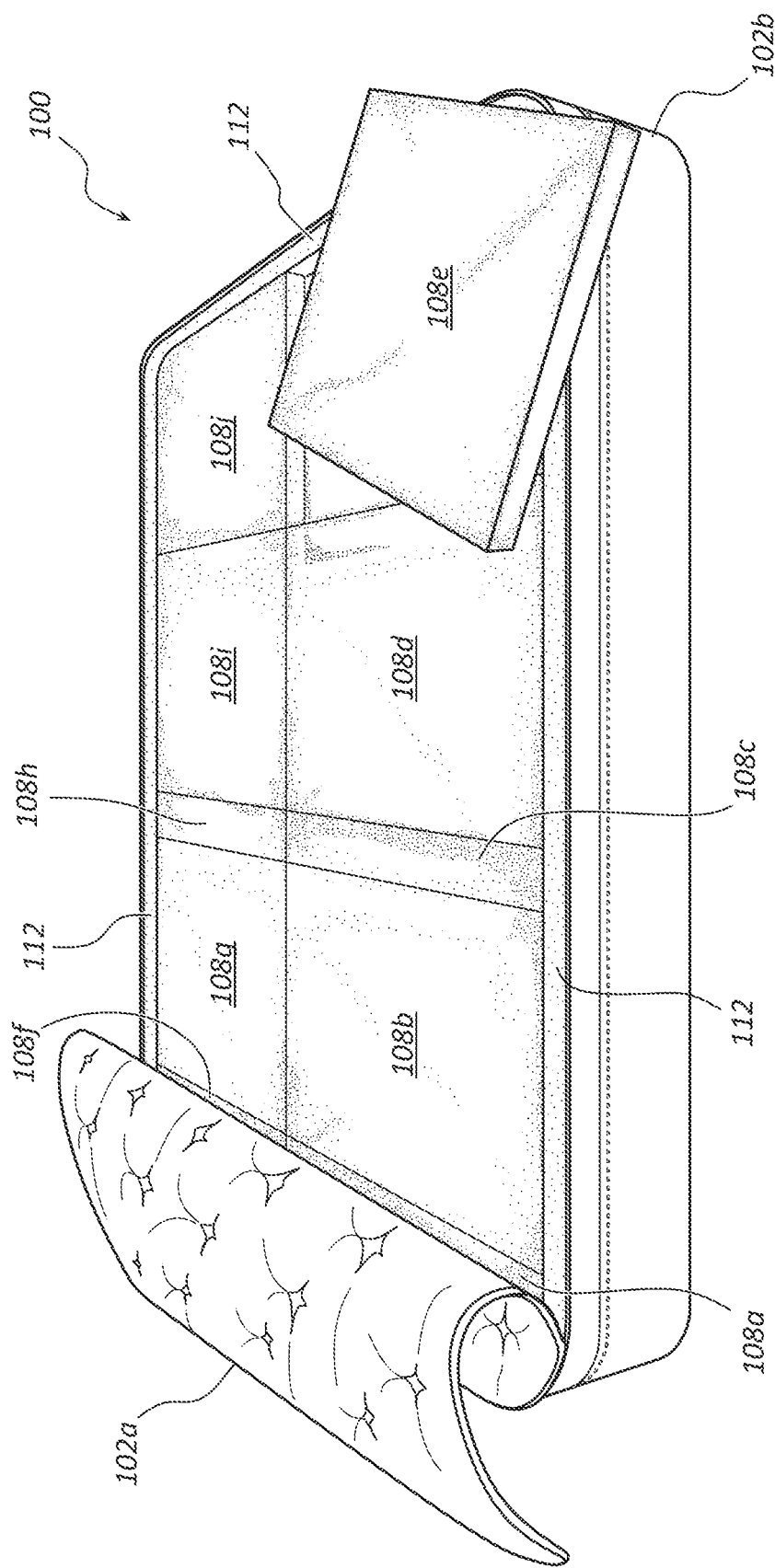
FIG. 10 illustrates the mattress of FIG. 9, where one of six pads has been removed.

While FIG. 2 may suggest the presence of "4" or "5" strips positioned in the lumbar region of the spine, Applicant has discovered that more often, slightly less support may be more appropriate (e.g., more typically "3" or "4" firmness values, or perhaps even a "2" for some users). In addition, sometimes a user may benefit from placement of a half-width strip (e.g., 2½ inches) in the lumbar location, rather than a 5 inch strip. It will be appreciated that the system allows a high degree of customization to each individual user, and also the ability to change things as the user tries out a particular configuration, and desires further adjustment. FIGS. 3, 9 and 10 show use of wider pads for most areas, with the narrower 5 inch strip under the lumbar region of the spine, with a spare strip positioned at the top of the bed. The spare strip could alternatively be placed at the foot of the bed. Such Figures illustrate that the pads and strips do not necessarily need to all be of the same width, and indeed, it can be beneficial (perhaps even critical to the support of the lumbar region) to provide a strip under the lumbar region that is narrower than the support layer pad positioned adjacent thereto.

FIGS. 3-6 show the mattress with the top cover removed (and where the bottom portion of the cover has actually also been removed in at least some of the views), showing the encasement with its sub-layer, and sidewalls extending upward and around the sub-layer, defining the recess (e.g., 2 inches deep) into which the strips 108 are to be placed. It is readily apparent from these Figures that the encasement includes further structure below the sub-layer (e.g., the pocketed coil springs).

While various other support structures are available in mattress construction, Applicant has found that fluid support structures (e.g., inflatable air bladders, water-bed systems and the like), as well as foam springs or the like do not provide adequate support to a user, particularly over time, as the mattress wears. Thus, Applicant prefers or even critically requires a construction that includes metal coil springs under the sub-layer of the encasement, with a foam pad support layer over the sublayer, which support layer actually provides variable firmness support to the user laying on the mattress. Such materials and construction are important differences over the various more "exotic" solutions available in the market today. Furthermore, the variable firmness support layer provided by foam pads or strips advantageously does not include any gaps between the individual pads and strips, such as might occur if circular or other rounded shape support members were used (e.g., as in a REVERIE mattress system). Applicant has found that the gaps inherent in such a system create an environment where it is simply not possible to provide adequate support to the user.

In addition, such "exotic" systems are quite expensive, as compared to the more standard foam support layer over pocketed coil springs construction that is most commonly used in traditional "non-exotic" mattresses. By using a similar construction, with a foam support layer over pocketed coil springs, but by dividing the foam support layer into a plurality of pads and strips, where each pad and strip can be removed, and interchanged with another pad or strip providing a different level of firmness, not only is the support layer now fully customizable to the unique needs of the user, but the mattress is also far more easily refurbished once the foam support layer wears out. For example, because the pads and strips of the foam support layer are easily accessible through a zippered or other selectively openable top cover, one may not only make adjustments to such a mattress as needed, but refurbish the mattress by replacing any or all of the foam pads or strips, once they wear out.

For example, a mattress with construction based on a typical foam support layer over pocketed coil springs may wear out after about 5 to 8 years. The present mattress systems address the replacement problem presented by such typical mattresses, offering an alternative system, that is easily refurbished. At an appropriate interval (which may depend on the weight or other characteristics of the user(s)), one may simply remove the foam strips, and replace them with new ones. Furthermore, in order to extend the life of the foam support layer, the user or another person may unzip the mattress cover, and flip the foam support layer pads and strips over, or interchange them with pads or strips of the same shape and number, located elsewhere in the mattress. Such actions may greatly extend the wear life of the foam layer pads and strips, much like rotating the tires on a car.

Another important feature is that the customization in firmness is not provided in the pocketed coil spring layer (which is too far down in the mattress, separated from the user lying on the bed by significant foam padding), but is in the top padding layer, directly under the zippered cover, so as to be best provide variations in firmness to the portions of the user's body requiring such. The pocketed coil springs may provide uniform firmness across the sleep surface, or the entire mattress, in contrast to a system such as in Howard, where customization is incorporated into the pocketed coil springs.

Because the mattress includes an overall construction that is similar to a conventional, "non-exotic" mattress with a foam support layer over pocketed coil springs, it can be provided at a cost that is very competitive to those types of mattresses, while providing customizability and refurbishability benefits that those mattresses do not enjoy. In addition, such a mattress will consistently and long term provide proper support to the lumbar region of the spine, as well as other regions of the user, fully customizable, as dictated by the clinical measurements (not user preference, which can be deceiving). Cost to refurbish such a mattress by replacing all of the foam pads and strips may only be about 10% to 50%, or 20% to 50% of the cost of the entire mattress. Because the other mattress components (e.g., the encasement, the pocketed coil springs, etc.) typically exhibit little or no wear for decades (e.g., 20-30 years, or even more), such a system is far more economical to own and maintain than the typical scenario where a user simply throws out a mattress after 5-10 years, and replaces it in its entirety. Such a mattress configuration also greatly reduces generation of waste associated with typical mattress disposal, as a result of its ability to be easily and quickly refurbished. For example, replacement and/or rotation of the pads and strips of the support layer does not even require that the mattress leave the bedroom of the user. Such refurbishment can easily be achieved in a matter of minutes, at the home of the user, and potentially by the user. Even evaluation of wear in the crush zone of the mattress, to ensure that no more than ¾ inch, or no more than ⅝ inch of compression or sag occurs during use can be performed by the user, at home.

In an embodiment, a coating may be applied to the HR foam pads or strips, or even the HD (high-density) foam of the encasement, if desired. KULKOTE is merely an example of such a coating that may be applied to any of the foam or other surfaces. KULKOTE is a temperature regulating coating, which absorbs and/or releases heat through a material in the coating that undergoes a phase change to effect the desired temperature regulation (i.e., keeping the sleeper warm when the environment is cold, and keeping the sleeper cool when the environment is hot).

The pads and strips of the foam support layer may be a resilient foam, such as latex foam. It an embodiment, it is not a memory foam, as such memory foams tend to provide support closer to that of fluid systems, which Applicants have found to be undesirable over the long term, particularly as it relates to efforts to maintain the spine in a properly supported, healthy orientation, with no more than ¾ inch, or no more than ⅝ inch compression particularly in the support layer pad or strip positioned under the lumbar region of the spine. Such foam materials are generally available and referred to in the art as either HR (high-resiliency) or HD (high density) foams. The support layer pads and strips may comprise the HR foam variety. The encasement is far more firm (even more firm than a "5" HR foam pad or strip), and may comprise the HD variety.

Although the pads and strips may be initially provided separately, in an embodiment, it may be desirable to actually attach the pads or strips together once the customized arrangement of has been determined. Thus, in an embodiment, the pads or strips may be glued, or otherwise attached to one another, so as to form a single piece at least with respect to the sleep surface provided by such an arrangement or assembly of pads and strips. For a mattress including two sleep surfaces, each arrangement may still remain separate and unattached to the adjacent arrangement. Alternatively, the two series of pads and strips (right and left on a queen or king mattress) may be attached together, as well. Such attachment of adjacent pads and strips may increase the wear durability of the foam pads or strips, although it also interferes with the ability to swap and flip pads, which swapping and flipping can greatly enhance pad and strip life. Depending on the strength of the adhesive or other attachment mechanism used, the pads or strips may later be able to be separated, if desired (e.g., to swap, flip or change the custom arrangement). If a very strong adhesive were used, such later separation may not be possible, as the foam may tear before the adhesive bond would break.

III. Examples Shown in Figures

FIG. 1 is an image of a mattress 100 that may include features as described herein. The image shows a mattress 100 that includes an outer cover 102 that can be visually customized to include a variety of colors schemes, logos, or other design aspects. As shown in FIG. 1, the outer cover 102 of the mattress 100 may be removable and cover substantially all of the mattress, including inner layers and other inner portions of the mattress, both top and bottom, as well as the sides. The outer cover 102 may be removably secured around the mattress via any number of securing methods. For example, in one implementation, the outer cover 102 may have a seam 104 that is zipped together (FIG. 2). While use of a zipper 106 may be preferred, it will be appreciated that other fasteners, e.g., including but not limited to hook and loop fasteners, such as Velcro, buttons, other clips or other means may alternatively be used.

The outer cover 102 (particularly the top thereof) may be easily and quickly removed to uncover the inside of the mattress. For example, a user may unzip the outer cover 102 to access inner layers of the mattress 100 that may need to be rotated, flipped, replaced, or to separately wash portions or all of the outer cover 102. Furthermore, in some implementations, the outer cover 102 may comprise multiple sections that can be removably secured together to form an outer covering of the mattress 100. For example, as seen in FIG. 2, the outer cover 102 may comprise a first portion 102a that covers only the top of the mattress 100, and a second portion 102b that covers the bottom and sides of the mattress 100. The first portion 102a may have a zipper 106 disposed around the outer perimeter thereof to be zipped together to the second portion 102b. The first and second portion may be zipped together to entirely cover the mattress 100. The first portion 102a may be unzipped and removed to expose the inner layers of the mattress 100 from the top, without removing the second portion 102b of the outer cover 102. While it may seem a minor thing, two zipper handles 106 may be provided, more easily allowing the user to unzip the half of the mattress desired. Such seemingly minor features can be important in ensuring that a user is able to make the needed rotations, replacements or similar changes, with as little hassle as possible, to improve compliance with any such needed schedule, to ensure that no more than ¾ inch or ⅝ inch of compression or sag occurs in the support layer pads or strips, particularly those in the central crush zone of the mattress (e.g., this is particularly critical for the support layer strip positioned under the lumbar region of the user's spine).

Also, as seen in FIG. 2, the outer cover 102 may at least partially comprise a relatively thin padded pillow top or quilted top. Such a top cover 102a may add to the comfort of the person sleeping on the mattress 100, although it is important that this top cover 102a not be so thick as to interfere with the prescriptive firmness values provided by the support layer (as the top cover 102a is positioned between the user lying on the mattress, and the support layer. By way of example, such top cover 102a may have a thickness of no more than 1 inch, or no more than ¾ inch, to ensure there is no "watering down" of the customized prescriptive firmness characteristics provided by the support layer located directly under such top cover 102a. In an implementation, the top portion 102a of the outer cover 102 (or "top cover") may be interchangeable with another top cover. For example, a user could quickly unzip, or otherwise remove, the top cover 102a from the rest of the outer cover 102 and zip a new top cover to the rest of the outer cover 102b, to better suit the user's needs.

FIG. 3 illustrates a mattress 100 similar to the mattress illustrated in FIG. 1, but with a schematic cut-away window on the side to illustrate the inner layers of the mattress 100, including a plurality of pads or strips 108a-108j disposed under the top cover 102a. As discussed above, the top cover 102a may comprise a relatively thinly padded layer, such as a quilted topper or other padded layer. This top cover 102a may be no more than about 1-inch thick.

The mattress 100 may have a support layer 108 disposed beneath the top cover that is about 2-inches thick and comprised of high-resilience (HR) foam (e.g., pads and strips 108a-108j). Foam materials in the art are typically either characterized as HR (high-resiliency) or HD (high density). In one implementation, the support layer 108 may include a plurality of individual pads and strips 108a-108j that extend across at least a portion of the top of the mattress 100. For example, in FIG. 3, the support layer 108 comprises 10 individual pads and strips (labeled 108a-108j). The pads and strips may be disposed between the top cover 102a and an encasement 110 comprised of high-density foam or other padded material, and held in place, at least in part, by the outer cover 102 (e.g., 102b). The foam layers 108a-108j may also be contained on top of the encasement 110 between sidewalls 112 that may extend up around the perimeter of the encasement 110, providing a firm seating edge, which is helpful to a user when sitting on the mattress edge, e.g., during entry and exit from the bed. Such a firm edge is particularly helpful to those with hip issues.

Figure 4:
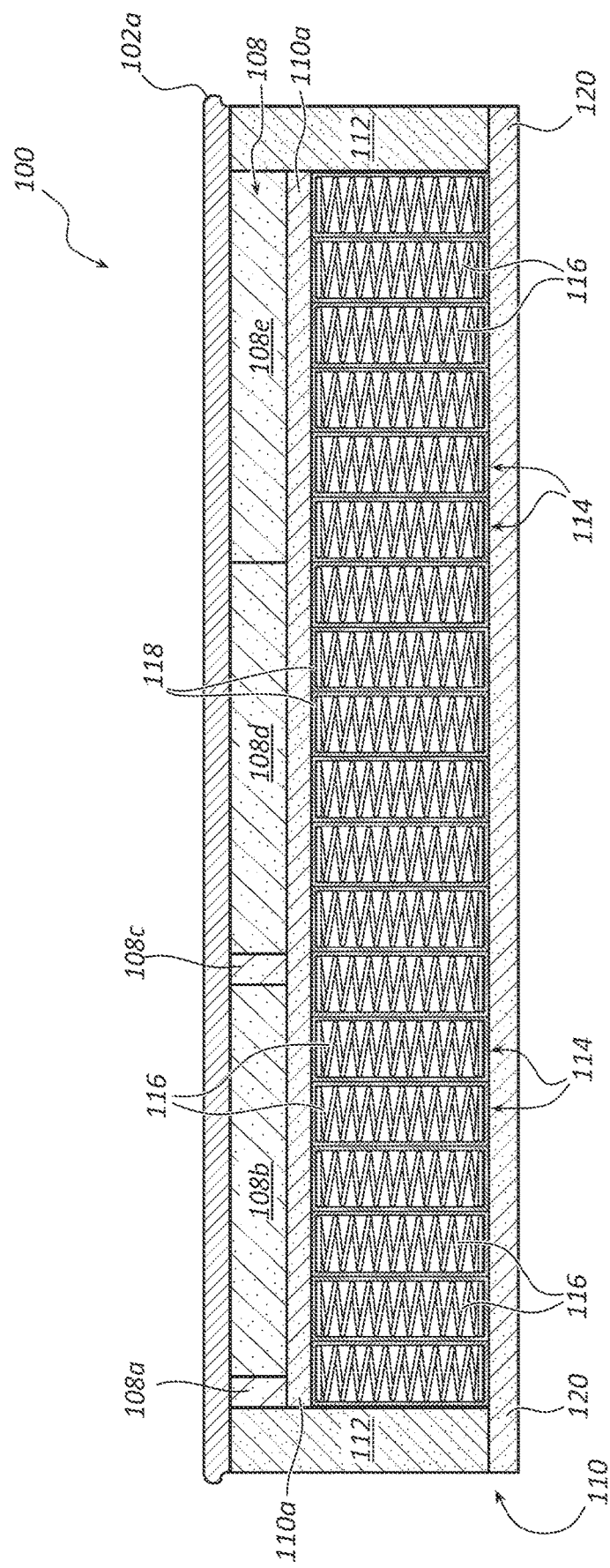
FIG. 4 illustrates a cross-sectional view of an implementation of a mattress.

FIG. 3 also illustrates a plurality of pocketed coil springs 114 disposed below the encasement 110. A pocketed coil spring 114 may include a metal coil spring 116 encased in a pocket of material 118, such as a fabric enclosure, as illustrated in FIGS. 3-4. The pockets 118 restrict the coil springs 116 from moving laterally, helping to hold them in place to be compressed vertically as a person lies on the bed. They also may allow individual pockets of springs 114 to be compressed independent of the degree of compression of an adjacent pocketed spring 114. Multiple springs 116 may be housed within a single fabric pocket 118, or a single spring 116 may be in a single pocket 118. A bottom layer of high-density foam 120 may be disposed below the pocketed coil springs 114 so as to provide added cushioning as well as prevent the coil springs 114 from directly contacting the ground or the bottom 102b of the outer cover 102 (e.g., reducing wear on the outer cover 102 that may otherwise occur if the encasement bottom layer 120 were not present). The pocketed coil springs provide a firm foundation to the mattress, with firm, uniform support across the entire mattress surface (or at least uniformity across a given sleep surface side of the mattress). Importantly, there is no attempt to introduce differences in firmness of support in the pocketed coil spring layer, which is too far down in the mattress, covered by significant padding, to have the needed effect of providing proper support to the user, particularly the lumbar region of the spine. Such is an important difference relative to the Howard reference. It is important that the variable, customized level of firmness be provided in the top portion of the mattress (e.g., covered only by the quilted top cover of the mattress), rather than positioning it below layers of padding having significant thickness.

Figure 5:
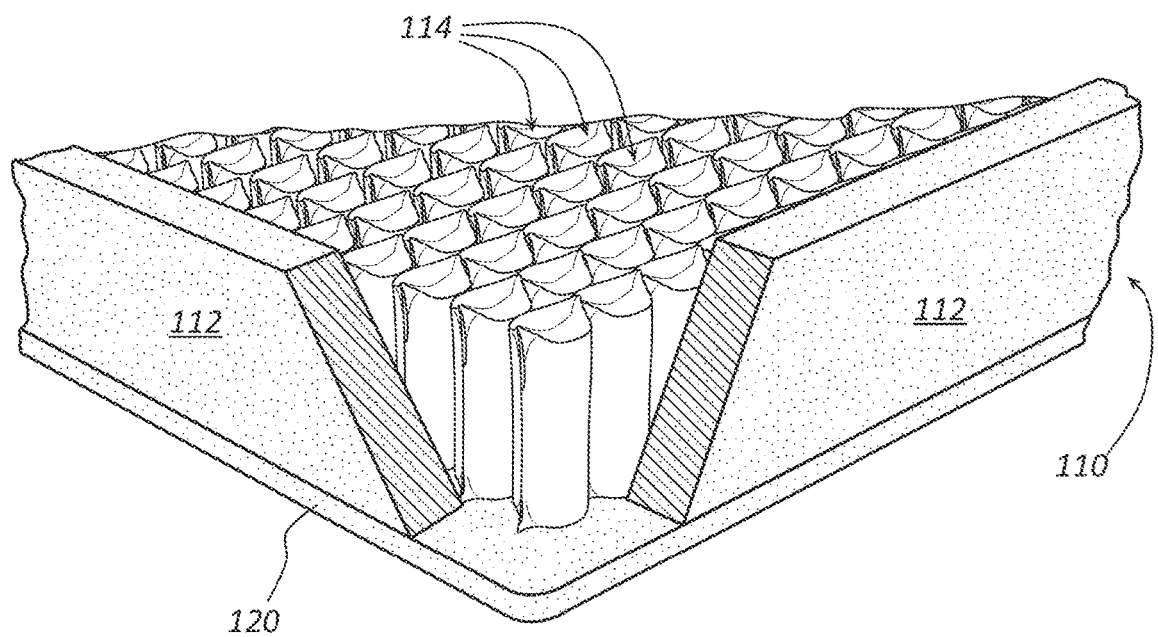
FIG. 5 illustrates a foam encasement of the mattress, which provides a supporting seating edge, where the encasement may be filled with pocketed coil springs.

Regarding various internal layers of the mattress, FIG. 4 illustrates a cross-sectional simplified schematic view of an implementation of a mattress 100 similar to that of FIG. 3, that includes a quilted top cover layer 102a, a customized firmness support layer 108 disposed beneath the top cover layer 102a (where the support layer 108 is configured as a plurality of foam pads and strips 108a-108j, separate from one another, as shown), an encasement sub-layer 110a beneath the support layer 108, where the encasement 110 may include sidewalls 112 extending around the foam pads 108a-108j of the support layer 108, and a plurality of pocketed coil springs 114 disposed beneath the sub-layer 110a of the encasement. The implementation illustrated in FIG. 4 includes a foam encasement 110 that extends around the perimeter of the plurality of pocketed coil springs 114. This is better illustrated in FIGS. 5 and 6, which FIG. 5 showing a corner of the encasement 110 cut away, to better see the pocketed coil springs 114. The foam encasement 110 may comprise a thickness of material that extends up to the same height as the springs 114 (see sidewalls 112) and extends around the perimeter of the mattress 100 to encase the plurality of pocketed coil springs 114. The foam encasement 110 may provide added structural support to an outer edge of the mattress, e.g., for sitting, as it is significantly stiffer than the support pad layer 108. Such a stiff, high density foam edge is helpful when entering or exiting the bed, particularly for users with hip conditions.

Figure 6:
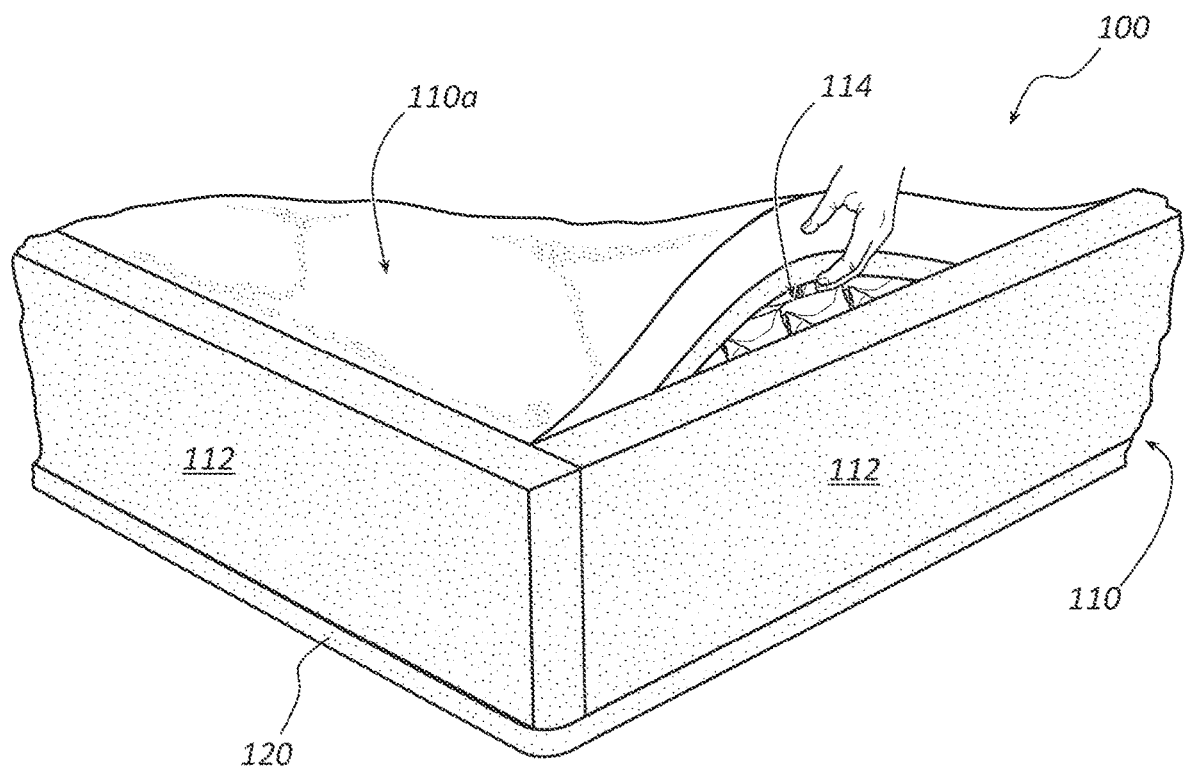
FIG. 6 shows another view into the encasement of the mattress, under the support pads, showing the pocketed coil springs.

The sub-layer 110*a* of the encasement may typically be from about 0.25" to 2" thick. The sidewalls 112 may be from about 1" to 3" thick. In FIGS. 5 and 6, the sublayer is 1" thick, and the sidewalls are 2" thick. Support layer 108 has been removed in these Figures to better show the structures beneath layer 108.

Returning to FIG. 3, the plurality of pads and strips 108*a*-108*j* that comprise the support layer 108 are arranged such that three pads and two strips (108*a*-108*e*) reside on a left side of the mattress 100 and three pads and two strips (108*f*-108*j*) reside on the right side of the mattress 100. This implementation of the mattress represents a typical division of pads that may accommodate two people sleeping on the bed. One person may sleep on the left, above pads 108*a*-108*e*, and another person may sleep on the right, above pads 108*f*-108*j*. The illustrated mattress 100 is a queen-sized mattress designed to accommodate two people. In one or more other implementations of the mattress, including large or smaller sized mattresses, such as twin-sized or king sized mattresses, the number and division of the pads may vary. For example, a twin-size mattress may only include 5 pads and strips total. A king size mattress may be similar to the queen-size mattress, including pads 108*a*-108*e* and 108*f*-108*j*.

In any case, each pad or strip may be removed and replaced, or rotated with another pad or strip to a different position within the mattress 100, where such pads or strips are of the same size (and firmness). For example: the first strip 108*a* can be moved to occupy the space where the other strip 108*c* is disposed to be positioned under the lumbar region of the user's spine. Such a configuration provides two lumbar strips, for periodic rotation, where the strip used for positioning under the lumbar region is taken from one location (e.g., above the head), at 108*a*, and positioned under the lumbar region of the spine, replacing strip 108*c*, e.g. when some compression of such strip becomes evident, and it would be beneficial to swap it out. In a similar manner, the second pad 108*b* can be moved to occupy the space where the fourth pad 108*d* is disposed; the fourth pad 108*d* can be moved to occupy the space of the fifth pad 108*e*, and the fifth pad 108*e* can be moved to occupy the space of the second pad 108*b*. The same rotations can be made on the other sleep surface side of the bed, with pads/strips 108*f*-108*j*. In addition to moving from one pad location to another, users may flip one or more of the pads over, to better spread the wear out.

Figure 7:
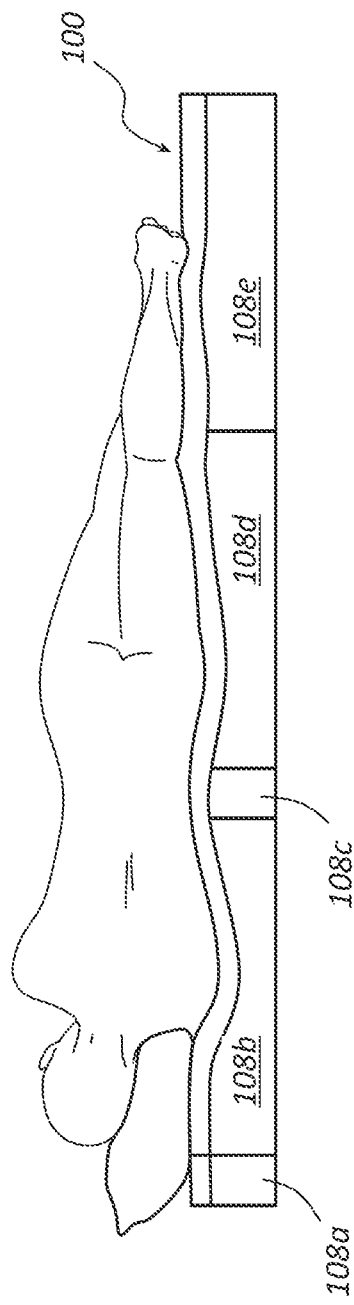
FIGS. 7-8 show how the rate and/or degree to which each pad wears down may depend on the sleeping position of the person sleeping on the mattress, as well as the rotatable position of the pad.
Figure 8:
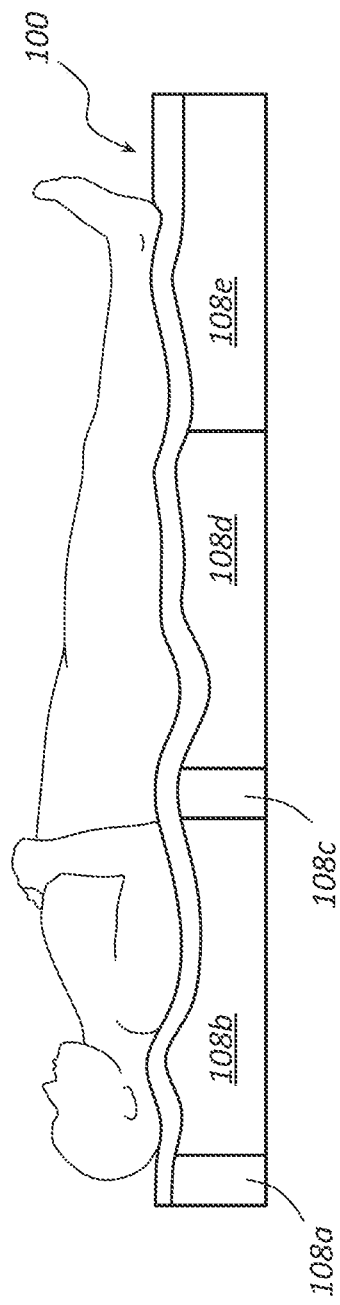

On this note, the different pads or strips may wear down or compress or sag to form depressions that result from permanent deformation or degradation of the pad material, particularly those in the central "crush zone" of the sleep surface of the mattress (e.g., the lumbar strip, and those pads/strips immediately on either side thereof). The rate and/or degree to which each pad or strip wears down may depend on the sleeping position of the people sleeping on the mattress 100, as well as the position of the pad or strip (i.e., 108*a*-108*j*). FIGS. 7 and 8 illustrate this concept. In any case, there will be significantly more deformation of the pads and strips in the central portion of the sleep surface, e.g., below the hips as compared to the deformation of the pad disposed beneath the head and lower legs and feet of the sleeper. Whether a person sleeps on their back or side (or even stomach) may produce similar results, with the greatest deformation (the crush zone) in the central portion of the sleep surface. For this reason, it is helpful to rotate the pads and strips throughout the different locations of the sleep surface and/or mattress, to provide more even wear across all pads and/or strips, to lengthen the service life of such members.

As stated above, the pads and strips of the support layer 108 may be made of a high-resilient foam that deforms elastically, so that the pads substantially return to shape once the person is no longer on the mattress 100, generally speaking. However, over time, the pads may form permanent or semi-permanent depressions caused by permanent deformation or other wear due to repeated compression from the weight of sleepers thereon. It is also the case that some foam materials may deform in a manner so that depressions formed in the pads may take more than the waking portion of a day, or even more than a week to fully return to their original, uncompressed shape free of depressions. Even with the return to the normal uncompressed shape, degradation may be occurring within the foam matrix structure of the pad, affecting the density, firmness, and other supportive characteristics of the pad over time, even where it may appear to exhibit no wear. In any case, because of the particular mattress construction, the user (or servicer) can remove the top cover 102*a* of the mattress 100 and periodically rotate and flip the pads and strips 108*a*-108*j* to allow the pads to wear more evenly over time.

For example, the pad supporting the sleeper's shoulders (e.g., position 108*b* or 108*g*) can be rotated through each of the other pad positions, so as to have approximately equal usage time e.g., under the feet of the sleeper. The lower legs and feet portion of the sleeper may be much lighter or provide lower pressure than the shoulder portion, so that the pad beneath the feet portion of the sleeper experiences much less deformation or wear. Thus, the pad under the feet portion of the sleeper can slowly return to its original shape, free of depression, over a sufficient period of time. In a similar manner, the spare lumbar strip 108*a* can be swapped with strip 108*d*, to extend the wear of the lumbar strips. This rotation of pads and strips can occur at any necessary repeated interval of time to ensure that each pad and strip is being worn evenly and given the opportunity to return to original form, maximizing the life of each pad and strip.

Furthermore, because of the particular configuration of the mattress 100, if any of pads 108*a*-108*j* become worn out, so that more than ¾ inch (or ⅝ inch) compression or sag is exhibited in any given pad (typically in the crush zones associated with lumbar strip 108*c* and pads 108*b*, 108*d* on either side thereof, and strip 108*h* and pads 108*g*, 108*i* on either side thereof), or a given pad no longer provides the desired degree of firmness, a user or servicer can replace one or more pads or strips with a new pad or strip. The pads can be replaced one-by-one as they wear out, or they can periodically be replaced all at once when the need arises, as determined by the condition of the pads, when the critical ¾ inch (or ⅝ inch) compression or "sag" has occurred, and/or with reference to the measurements taken of the user's spinal curvature (e.g., particularly how such curvature may be changing over time, as periodically measured). For example, the present methods and systems would allow a user to simply replace all of the support layer pads 108*a*-108*j* at a given interval (such as a 4 year interval, or even a far shorter interval, such as 3 months, or 6 months, or 1 year, or 2 years, or 3 years), at far lower expense than the cost and effort of replacing the entire mattress. For example, such pad replacement may be accomplished at only 5% to 50%, 10% to 50%, or 20% to 50% of the typical cost of total mattress replacement. For example, such pad replacement may cost less than 10%, or less than 20% of the comparative cost to replace the entire mattress.

Therefore, in one implementation of the present disclosure, a method for maintaining a mattress can include: at least partially removing a top layer 102a of the mattress 100; rotating or otherwise repositioning one or more of a plurality of individual pads and strips 108a-108j disposed below the top layer 102a of the mattress 100; and re-securing the top layer 102a of the mattress 100 over the plurality of pads. In another implementation, the method may include: at least partially removing a top layer 102a of the mattress 100; replacing one or more of a plurality of pads or strips 108a-108j disposed below the top layer 102a of the mattress 100; and securing the top layer 102a of the mattress 100 over the plurality of pads Advantageously, the support layer 108 made up of pads/strips 108a-108j which is customized in firmness is in the top portion of the mattress, so as to be directly accessible once the top layer 102a is unzipped. In other words, there are no padding or other layers over such customized layer, also needing to be removed, so as to make access to such customized layer as easy as possible.

These methods are illustrated in FIGS. 9-10. FIG. 9 illustrates a mattress 100 that includes a top cover 102a that has been at least partially removed to expose a plurality of support layer pads 108a-108j. FIG. 10 illustrates one of six pads (pad 108e) that has been removed. This pad may either be rotated to a new position or replaced by a new pad. Rotation of the pads may proceed as outlined herein in conjunction with FIG. 3, where strip 108a moves to the position of strip 108c, strip 108c moves to the position of strip 108a, pad 108b moves to the position of pad 108d, pad 108d moves to the position of pad 108e, and pad 108e moves to the position of pad 108b. A similar rotation may occur on the opposite side of the bed. Where pads or strips are of the same size and firmness, rotation could also occur between sides (e.g., any pads/strips 108a-108e may be swapped with appropriate pads/strips 108f-108j). In addition to or alternative to such movement, the pads could be flipped over. Preferably, pads may be both moved and flipped at the same time. Such repositioning (e.g., "rotation") of the pads and strips may be performed according to a preset schedule, e.g., once per week, twice per month, once per month, or the like. The particular period between such rotation may depend on what best extends life of the pads and strips, while not being overly burdensome to the user or other servicer making the changes.

Figure 11:
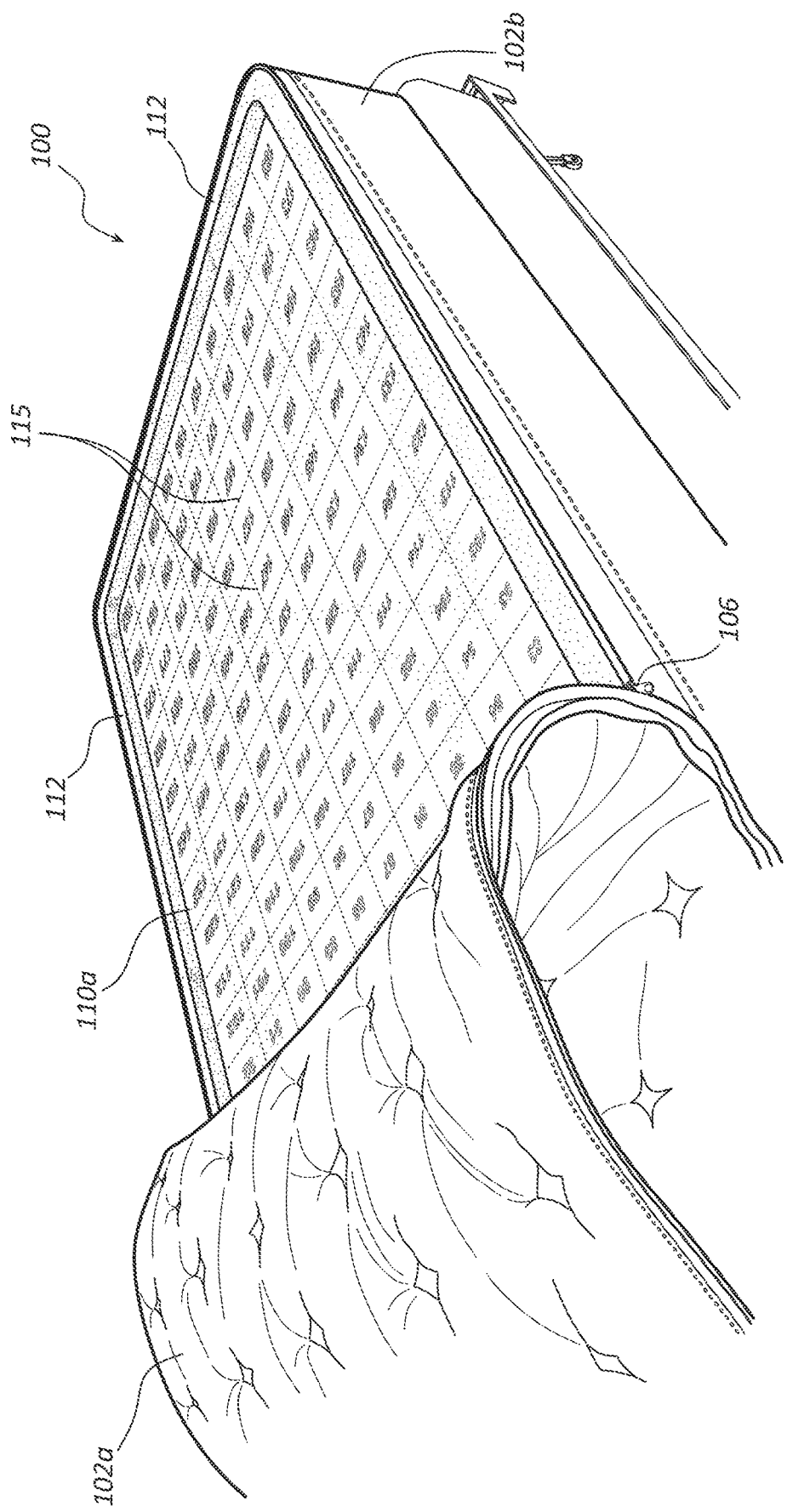
FIG. 11 shows the mattress with the top cover partially removed and all the support layer pads removed.

FIG. 11 shows a mattress 100 with a top cover 102a that has been partially removed and all the support layer pads and strips 108a-108j removed. Thus, the encasement 110, including a perimeter sidewall 112 configured to maintain the positions of the pads as described above, is visible. New support layer pads and strips may be placed therein or the pads and strips that were removed may be place therein in different positions, as described in detail above. It is important that the pads and strips 108a-108j be visible, and removable, simply by unzipping the top cover 102a, so as to facilitate easy servicing of the mattress 100. No layers or materials are present between top cover 102a and support layer 108, so that removal of any additional layers is not required. In addition to ease of servicing, this configuration of positioning the customizable support layer 108 in the top portion of the mattress 100 is important, as it ensures that the customized firmness characteristics provided by support layer 108, which are based on the measured spinal curvature of the patient, are not "diluted" by placement of additional padding of significant thickness between such support layer 108 and the top cover 102a. Such is an important characteristic of the present invention, e.g., as compared to Howard, or similar references that suggest use of a customized firmness layer in the coil springs, but provide significant padding over such customized layer, between such layer and any top cover, which defeats any prescriptive benefit provided by such a customized firmness layer.

Because of the particular configuration, a user or servicer can easily and quickly rotate the support layer pads and strips to maintain and recondition the mattress, without having to fully replace the mattress. Replacing one or all of the pads or strips may be significantly less expensive than replacing the entire mattress, which may greatly reduce the costs of maintenance. As discussed above, the other layers, including the coil springs 114, likely do not need to be replaced when the support layer pads and strips 108a-108j are replaced, so that only replacing the support layer pads 108a-108j may be cost effective and require less labor than total mattress replacement. It will be apparent that various configurations are possible, although the illustrated 10 pad/strip configuration may be particularly beneficial, as it facilitates providing a thinner lumbar support strip for positioning under the lumbar region of the user, so as to provide significantly higher firmness here, with a space such strip also in the same sleep surface, above the head (could alternatively be positioned at or below the legs or feet), with 3 other larger pads, for rotation through the various positions.

The mattress pads and strips 108a-108j may be numbered, color coded, or otherwise provided with identifying indicia to inform a user as to the firmness of any given mattress pad or strip. For example, HR pads may be stocked in firmness values of from 1-5, where 1 is very soft, and 5 is very firm. In a typical bed, all of pads 108b, 108d, and 108e (as well as 108g, 108i, and 108j) may be a firmness value of "2", or "1". The lumbar strips 108a, 108c, 108f and 108h may be of greater firmness, such as "3", "4" or even "5".

Any of the pads or strips as described herein may be covered or otherwise treated with a fire retardant material, or other treatment material. For example, in an embodiment, a "fire sock" or other sock may be provided to cover the pad. Such a covering could be removable, e.g., and washable. In another embodiment, no such sock or covering may be provided (i.e., pads could be "raw").

The removable cover 102a associated with a mattress as described herein, may be configured to be replaced as needed, and may be launder-able (e.g., it may include minimal or no foam, only batting therein, facilitating easier laundering of the removable cover). Where any foam layer is included in such cover 102a, it may be no more than 1 inch, or no more than 0.5 inch thick, particularly where it may have a quilted texture, decreasing its thickness. The removable cover may have built-in waterproof protection layer (e.g., no separate waterproof mattress pad required).

In an embodiment, the pocketed coil springs may include extra coils (e.g., increased coil density) under the crush zone of the mattress for added support. Such an option may aid in increasing the wear durability of a mattress, as these regions of the mattress generally see the most wear. Such increased firmness or support under the crush zone, in the pocketed coil spring layer is not a substitute for providing customization in the support layer 108, which must be positioned in the top portion of the mattress, directly under the top cover 102a.

As a refurbishment option, the encasement 110, outer covering 102, or any of the foam pads or strips 108a-108j or other foam layers may be replaced as needed, instead of purchasing an entire new mattress. Even though such a method and system may require shipping expenses, the overall cost of such a system will be significantly less than that associated with complete mattress replacement.

Assessment of the degree of wear of the pads of the mattress may be determined using any suitable method. In an embodiment, such assessment may be achieved using a ruled stand, a laser, and a weighted target (or some combination of such items). The quality characteristics and resilience of the foam are able to be determined, including determination as to whether the foam pad is showing any collapse or decrease in ability to support the weight of a typical human body laying thereon, as would be typical during use of the mattress. The results of such assessment can be used to determine when to replace any given pad, i.e., if there is more than ¾ inch, or more than ⅝ inch compression within the lumbar strip, or another pad.

Figure 12:
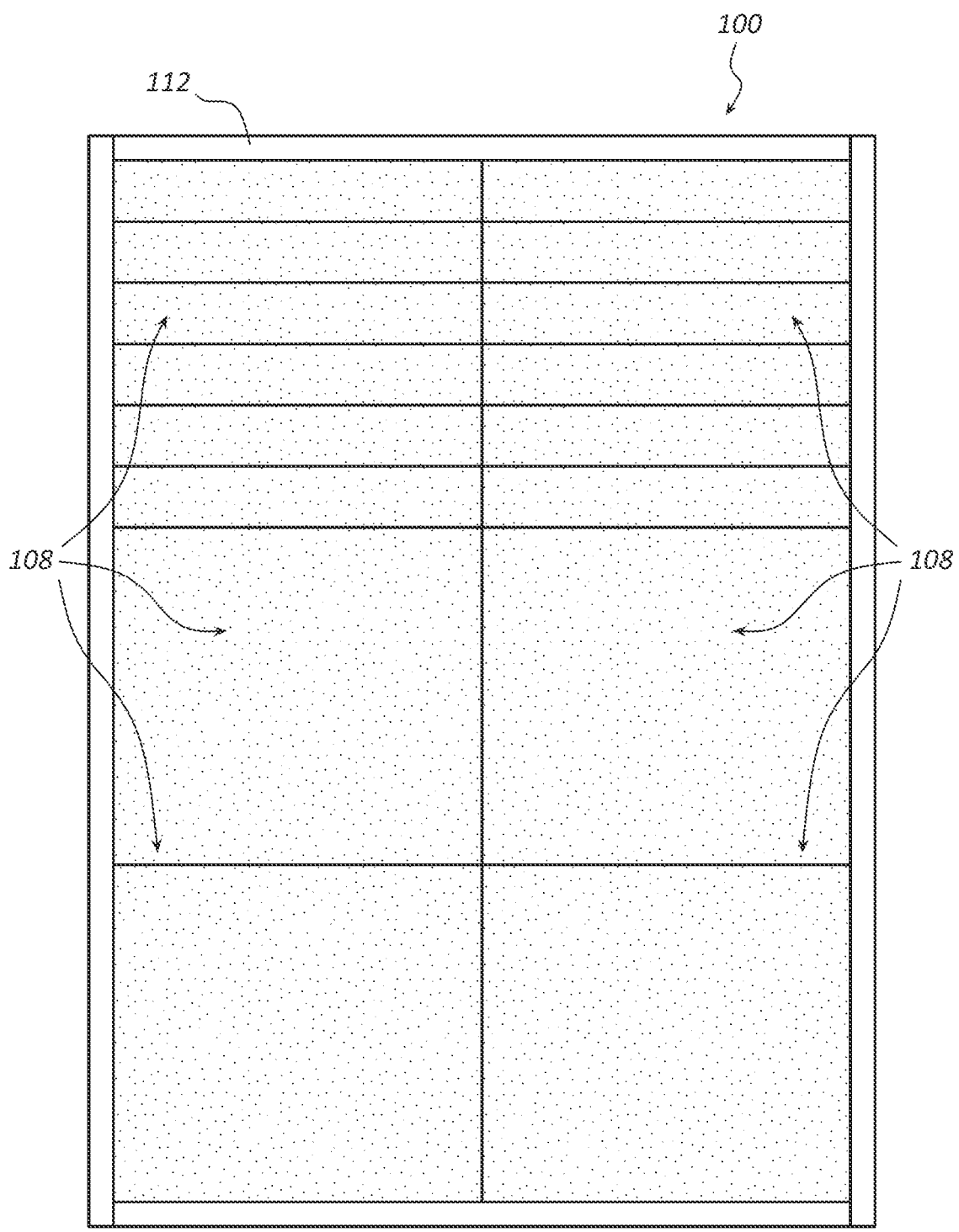
FIG. 12 shows another support layer configuration, for the mattress.

FIG. 12 illustrates another configuration, where the support layer 108 is somewhat differently configured, to include one less large pad per sleep surface, being replaced by a series of strips. Such may accommodate additional specific anatomical support needs of the particular person sleeping on the mattress, at locations other than just under the lumbar region of the spine (e.g., under the shoulders, and/or neck, as well). The principles of operation are the same, where measurements can be taken of the spinal curvature within these upper spinal regions (e.g., corresponding to the shoulders and/or neck), and selection of the appropriate firmness support strips made, to accommodate the prescriptive need.

FIG. 11 further shows how the sub-layer 110a of the encasement 110 can include a grid 115 imprinted on the sub-layer, to help guide prescription fitting and discussions between the patient user and the mattress provider (practitioner) relative to support management.

As noted herein, the ability to ensure that no more than ¾ inch of compression or sag occurs in the central crush zone of the mattress (e.g., particularly in the support layer strip positioned under the lumbar region of the user's spine) is critical to the present invention. The degree to which any such compression or sag occurs can be measured by various techniques, which will be apparent to those of skill in the art, in light of the present disclosure. A non-limiting exemplary methodology is described below.

Clinical Relevance. Sagging mattresses promote chronic bulging of lumbar discs. Bulging discs lose inflation and ability to expand firmly against upper and lower vertebrae, thus reducing spine stability at that level. The sleeping, unstable spine is subjected to gravitational sheer forces that insidiously draw susceptible vertebra downward from between their neighbors, threatening dislocation and forcing spine stabilizing muscles to work harder. The greater the sag, the greater the threat of damage to intervertebral discs. The greater the disc damage, the greater the instability and the less mattress sag the compromised spine can tolerate before pain and spasm attack. Clinical research by Applicant reveals that patients with an unstable lumbar spine segment can tolerate no more than 16 mm (⅝") or in the best case, no more than 19 mm (¾ inch) of mattress sag before reporting pain.

Laboratory Sag Measurement. Mattress sag is typically found in the center of used mattresses where most of the sleeper's mass is located (i.e., the crush zone). It can be objectively evaluated by placing a weighted target at each cell (e.g., by placing a fitted sheet with a grid as in FIG. 11 over the mattress) and then measuring how deeply the target settles into the mattress using a laser and vertical rule. Comparing all resulting cell measurements identifies the location(s) and maximum depths of all mattress sagging.

Home Sag Measurement. Where a laser and rule may not be readily available, more practical sag measurement can be accomplished at home by a user using three equal weights and a straight rod such as a mop handle. The weights can be milk jugs containing six pints of water or cans of dried beans, weighing about six pounds each. Such weights (and resulting psi pressure values) approximate that of a typical user laying on the mattress. Although unweighted measurement using a simple string pulled tightly from head to foot also works, weighted measurement is more accurate because it overcomes any irregularities of the quilted mattress top cover. Placing the weights in a straight line that includes the obvious center of mattress sagging and laying the rod across the three weights reveals the depth of the sag.

Results. Measurement of new mattresses finds no sag because the undamaged topper and foam support layer receive the three weights uniformly. Unfortunately, all foam materials are mostly air and begin to compress with use. Standard mattress foam begins to fail within weeks of use while high quality foams may last several months before they show evidence of collapsing. An exemplary mattress constructed of medium grade foam developed 18 mm of sag within 12 months. Within 16 months both husband and wife arose each morning with more low back pain than they could tolerate, and the mattress was replaced. The present inventive mattress and methods address such issues.

Back pain patients who are able to tolerate only 16 mm of mattress sag are typically patients with chronic, recurring discomfort associated with a diagnosis of Degenerative Disc Disease ("DDD"). DDD is a medical label for what is really mechanical wear and tear, and is actually a condition, not a disease. The condition is mechanical, not medical, and correction must also be mechanical. Since the condition is worsened by gravitational shearing, mechanical correction must remain present to prevent the shearing as long as shearing forces are present.

Conclusion. Mattress sag adversely affects the integrity and stability of the human spine, especially the lumbar spine. The deeper the sagging of a mattress, the greater the damaging effect upon the spine's discs, joints, and muscles. Correction requires the accomplishment of two fundamental goals: 1) increase the integrity and stability of the spine, especially the lumbar spine, and 2) eliminate as much mattress sagging as possible, with 19 mm (¾ inch), more preferably 16 mm (⅝ inch) being the critical limit.

The present invention can be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

The invention claimed is:

1. A method for customizing support provided by a plurality of portions of a mattress to an individual user, the method comprising: measuring a curvature of a spinal region of a person's back; providing a customizable mattress including: a top cover removably attached to a remainder of the mattress by a zipper; an encasement extending beneath the top cover and having a sidewall extending up and around an outer perimeter of the encasement; a customizable support layer comprising a plurality of support layer foam pads or strips disposed in the encasement, on a sub-layer of the encasement so that the sidewall of the encasement extends around an outer perimeter of the plurality of support layer foam pads or strips, wherein at least one of the support layer foam pads or strips provides a different level of firmness relative to a level of firmness provided by another of the support layer foam pads or strips, and wherein each of the support layer foam pads or strips are individually removable from the encasement; and a plurality of pocketed coil springs below a sub-layer of the encasement, wherein the pocketed coil springs are uniformly configured to provide a uniform level of firmness across the sub-layer of the encasement; and selecting and positioning the plurality of support layer foam pads or strips into the encasement, on the sub-layer, in a customized arrangement customized to the individual user, to provide different firmness characteristics for the user from head to foot, wherein selection and positioning of the support layer foam pads or strips is based on the measurement of the curvature of the spinal region of the person's back, such that a sleep surface is custom created in which the support layer foam pads or strips provide different levels of firmness to different regions of the user's body from head to foot when laying on the mattress, based on the measurement of the curvature of the spinal region of the person's back, wherein a support layer strip positioned under a lumbar region of the user's spine ensures that no more than ¾ inch of compression occurs during use by said user; wherein the support layer strip positioned under the lumbar region of the user's spine has a greater firmness and a narrower width than that of adjacent pads or strips so that the support layer strip positioned under the lumbar region of the user's spine is configured to ensure that no more than ¾ inch of compression occurs during use, so as to maintain and/or improve spinal curvature relative to a desired idealized spinal curvature.

2. The method of claim 1, wherein the sub-layer of the encasement includes a grid imprinted thereon, to help guide prescription fitting and discussions with the user relative to support management.

3. The method of claim 1, wherein the support layer foam pads or strips include two support layer foam strips, one being the support layer strip positioned under the lumbar region of the user's spine, and the other being of identical firmness, size and shape, so as to be a spare lumbar support layer strip, the spare lumbar support layer strip being positioned either above the head, or under the legs or feet of the user.

4. The method of claim 1, wherein the support pads and strips comprise three pads and 2 strips, per sleep surface of the mattress.

5. The method of claim 1, wherein the mattress is a king or queen mattress providing two sleep surfaces, wherein the top cover is attached over the mattress with two independent zippers, so as to allow a user to access the support layer foam pads or strips of each sleep surface independently of the support foam pad strips of the other sleep surface.

6. The method of claim 1, wherein measurement of the curvature of the spinal region of the person's back is relative to an idealized curvature for that person.

7. The method of claim 6, further comprising following up with the individual user to remeasure the curvature of the spinal region of the person's back, the method further comprising unzipping the top cover of the mattress, and replacing at least one of the support layer foam pads or strips with another support layer foam pad or strip that provides a different level of firmness relative to the replaced support layer foam pad or strip.

8. The method of claim 7, further comprising implementing the following steps, or instructing the user to implement the following steps:
unzip the top cover of the mattress;
flip each of the support layer foam pads and strips over so as to provide more even wear to the pads and strips; and
swap support layer foam pads and strips of the same firmness, shape, and size from different locations in the encasement to provide more even wear to the pads and strips, and
zip the top cover closed over the mattress again.

9. The method of claim 8, wherein the mattress includes 2 sleep surfaces, each with a customizable support layer, the method further comprising measuring the curvature of a spinal region of the person's back for 2 users, the method further comprising customizing each respective support layer to each respective user, and wherein the customized arrangement customized to each of the 2 users for the support layer foam pads and strips in each customizable support layer are different from one another.

10. The method of claim 1, wherein the support layer strip positioned under a lumbar region of the user's spine ensures that no more than ⅝ inch of compression occurs during use by said user.

11. The method of claim 1, further comprising measuring the compression in the support layer strip positioned under a lumbar region of the user's spine, the method further comprising replacing the support layer strip positioned under the lumbar region of the user's spine when ¾ inch or more of compression has occurred.

12. The method of claim 1, further comprising measuring the compression in the support layer strip positioned under a lumbar region of the user's spine, the method further comprising replacing the support layer strip positioned under the lumbar region of the user's spine when ⅝ inch or more of compression has occurred.

13. A method for customizing support provided by a plurality of portions of a mattress to an individual user, the method comprising: measuring a curvature of a spinal region of a person's back; providing a customizable mattress including: a top cover removably attached to a remainder of the mattress by a zipper; an encasement extending beneath the top cover and having a sidewall extending up and around an outer perimeter of the encasement; a customizable support layer comprising a plurality of support layer foam wider pads and narrower strips disposed in the encasement, on a sub-layer of the encasement so that the sidewall of the encasement extends around an outer perimeter of the plurality of support layer foam pads and strips, wherein at least one of the support layer foam pads or strips provides a different level of firmness relative to a level of firmness provided by another of the support layer foam pads or strips, and wherein each of the support layer foam pads and strips are individually removable from the encasement; wherein the customizable support layer is positioned directly under the top cover, so as to be directly accessible once the top cover is unzipped, without requiring removal of any further layers positioned between the customizable support layer and the top cover; and a plurality of pocketed coil springs below a sub-layer of the encasement; and selecting and positioning the plurality of support layer foam pads and strips into the encasement, on the sub-layer, in a customized arrangement customized to the individual user, to provide different firmness characteristics for the user from head to foot, wherein selection and positioning of the support layer foam pads and strips is based on the measurement of the curvature of the spinal region of the person's back, such that a sleep surface is custom created in which the support layer foam pads and strips provide different levels of firmness to different regions of the user's body from head to foot when laying on the mattress, based on the measurement of the curvature of the spinal region of the person's back, wherein a support layer strip positioned under a lumbar region of the user's spine ensures that no more than ¾ inch of compression occurs during use by said user; wherein the support layer strip positioned under the lumbar region of the user's spine has a greater firmness and a narrower width than that of adjacent pads or strips so that the support layer strip positioned under the lumbar region of the user's spine is configured to ensure that no more than ¾ inch of compression occurs during use, so as to maintain and/or improve spinal curvature relative to a desired idealized spinal curvature.

14. A mattress providing customized support to an individual user, the mattress comprising: a top cover removably attached to a remainder of the mattress by a zipper; an encasement extending beneath the top cover and having a sidewall extending up and around an outer perimeter of the encasement; a customizable support layer comprising a plurality of support layer foam pads or strips disposed in the encasement, on a sub-layer of the encasement so that the sidewall of the encasement extends around an outer perimeter of the plurality of support layer foam pads or strips, wherein at least one of the support layer foam pads or strips provides a different level of firmness relative to a level of firmness provided by another of the support layer foam pads or strips, and wherein each of the support layer foam pads or strips are individually removable from the encasement, each of the support layer foam pads or strips being positioned in the encasement based on a measured curvature of a spinal region of the individual user's back; and a plurality of pocketed coil springs below a sub-layer of the encasement; and wherein the plurality of support layer foam pads or strips are positioned into the encasement, on the sub-layer, in a customized arrangement customized to the individual user, to provide different firmness characteristics for the user from head to foot, wherein selection and positioning of the support layer foam pads or strips is based on measurement of the curvature of the spinal region of the individual user's back, such that a sleep surface is custom provided in which the support layer foam pads or strips provide different levels of firmness to different regions of the user's body from head to foot when laying on the mattress, based on the measurement of the curvature of the spinal region of the individual user's back, wherein a support layer strip positioned under a lumbar region of the user's spine ensures that no more than ¾ inch of compression occurs during use by said individual user; and wherein the support layer strip positioned under the lumbar region of the user's spine has a greater firmness and a narrower width than that of adjacent pads or strips so that the support layer strip positioned under the lumbar region of the user's spine is configured to ensure that no more than ¾ inch of compression occurs during use, so as to maintain and/or improve spinal curvature relative to a desired idealized spinal curvature.

15. The mattress of claim 14, wherein the pocketed coil springs are uniformly configured to provide a uniform level of firmness across the sub-layer of the encasement.

16. The mattress of claim 14, wherein the support layer foam pads or strips include two support layer foam strips, one being the support layer strip positioned under the lumbar region of the user's spine, and the other being of identical firmness, size and shape, so as to be a spare lumbar support layer strip, the spare lumbar support layer strip being positioned either above the head, or under the legs or feet of the user.

17. The mattress of claim 16, wherein the support pads and strips comprise three pads and 2 strips, per sleep surface of the mattress.

18. The mattress of claim 14, wherein the support layer strip positioned under the lumbar region of the user's spine ensures that no more than ⅝ inch of compression occurs during use by said individual user.

19. The mattress of claim 14, wherein the mattress is a queen or king mattress including 2 sleep surfaces, each with a customizable support layer, wherein an arrangement of the pads and strips in each customizable support layer are customized individually to two individual users, with each of the two customizable support layers being differently configured from one another, each based on the measured curvature of the spinal region of each of the two individual user's back's.

20. The method of claim 1, wherein the customizable support layer is within a top 3 inches of the mattress.

\* \* \* \* \*